(12) United States Patent
Laub et al.

(10) Patent No.: US 7,981,865 B2
(45) Date of Patent: Jul. 19, 2011

(54) ANTIGENIC FRAGMENTS OF HUMAN FACTOR VIII POLYPEPTIDES

(75) Inventors: Ruth Laub, Brussels (BE); Mario Di Giambattista, Braine-le-Comte (BE)

(73) Assignee: Department Central De Fractionment De La Croix-Rouge Scrl, Brussels (BE)

( * ) Notice: Subject to any disclaimer, the term of this patent is extended or adjusted under 35 U.S.C. 154(b) by 775 days.

(21) Appl. No.: 11/267,631

(22) Filed: Nov. 3, 2005

(65) Prior Publication Data

US 2006/0051367 A1   Mar. 9, 2006

Related U.S. Application Data

(63) Continuation of application No. 09/853,080, filed on May 9, 2001, now abandoned, which is a continuation-in-part of application No. 08/765,837, filed as application No. PCT/BE95/00068 on Jul. 14, 1995, now Pat. No. 6,866,848.

(30) Foreign Application Priority Data

Jul. 14, 1994 (BE) ..................................... 9400666

(51) Int. Cl.
*A61K 39/00* (2006.01)
(52) U.S. Cl. .... 514/14.3; 530/326; 530/806; 424/140.1; 435/7.1; 435/7.92
(58) Field of Classification Search .......................... None
See application file for complete search history.

(56) References Cited

U.S. PATENT DOCUMENTS

| | | | |
|---|---|---|---|
| 4,965,199 A | 10/1990 | Capon et al. | |
| 6,866,848 B2 * | 3/2005 | Laub et al. ................. | 424/185.1 |

FOREIGN PATENT DOCUMENTS

| | | |
|---|---|---|
| EP | 0202853 | 11/1986 |
| JP | 62012722 | 1/1987 |
| WO | WO 88/00831 | 2/1988 |
| WO | WO 9602572 A2 * | 2/1996 |
| WO | WO 00/34317 | 6/2000 |
| WO | WO 02060917 A2 * | 8/2002 |

OTHER PUBLICATIONS

Foster et al., Blood, 1990, 75:1999-2004.*
Foster et al., J. Biol. Chem., 1988, 263:5230-5234.*
Levinson et al., Genomics 1992, 14:585-589.*
Campbell, A., Monoclonal Antibody Technology, 1984, Elsevier Science Publishers, pp. 1-32.*
Algiman, M., et al. (1992) Natural antibodies to factor VIII (antihemophilic factor) in healthy individuals. Proc. Natl. Acad. Sci. USA 89:3795-3799.
Dietrich, G., et al. (1992) Origin of Anti-idiotypic Activity Against Anti-factor VIII Autoantibodies in Pools of Normal Human Immunoglobulin G (IVIg). Blood 79:2946-2951.

Ewenstein, B. M., et al. (2000) Inhibition of CD40 ligand (CD154) in the treatment of factor VIII inhibitors. Haematologica 85 (Suppl. 10):35-39.
Foster, P. A. et al. (1989) Factor VIII Structure and Function. Blood Reviews 3:180-191.
Janin, J. (1979) Surface and inside volumes in globular proteins. Nature 277:491-492.
Karplus, P. A. et al. (1985) Prediction of Chain Flexibility in Proteins. Naturwissenschaften 72:212-213.
Knobl, P. and Derfler, K. (1999) Extracoporeal Immunoadsorption for the Treatment of Haemophilic Patients with Inhibitors to Factor VIII or IX. Vox Sanguinis 77 (Suppl. 1):57-64.
Laub, R., et al. (1999) Inhibitors in German Hemophilia A Patients Treated with a Double Virus Inactivated Factor VIII Concentrate Bind to the C2 Domain in FVIII Light Chain. Thromb. Haemost. 81:39-44.
Lollar, P. (2000) Mapping factor VIII inhibitor epitopes using hybrid human/porcine factor VIII molecules. Haematologica 85 (Suppl. 10):26-30.
Moreau, A., et al. (2000) Antibodies to the FVIII light chain that neutralize FVIII procoagulant activity are present in plasma of nonresponder patients with severe hemophilia A and in normal polyclonal human IgG. Blood 95:3435-3441.
Morrisson, A. E. and Ludlam C. A. (1995) Acquired Haemophilia and its Management. Br. J. Haematol. 89:231-236.
Palmer, D. S., et al. (1997) Identification of Novel Factor VIII Inhibitor Epitopes using Synthetic Peptide Arrays. Vox Sanguinis 72:148-161.
Parker, J. M. R., et al. (1986) New Hydrophilicity Scale Derived from High-Performance Liquid Chromatography Peptide Retention Data: Correlation of Predicted Surface Residues with Antigenicity and X-ray-Derived Accessible Sites. Biochem. 25:5425-5432.
Peerlinck, K., et al. (1997) Factor VIII Inhibitors in Previously Treated Haemophilia A Patients with a Double Virus-inactivated Plasma Derived Factor VIII Concentrate. Throm. Haemost. 77:80-86.
Pemberton, S., et al. (1997) A Molecular Model for the Triplicated A Domains of Human Factor VIII Based on the Crystal Structure of Human Ceruloplasmin. Blood 89(7):2413-2421.
Pratt, K. P. (2000) Relating structure to function: The role of the C2 domain in Factor VIII. Curr. Opinion Drug Discovery & Development 3(5):516-526.
Raut, S., et al. (1998) Modification of Factor VIII in Therapeutic Concentrates after Virus Inactivation by Solvent-Detergent and Pasteurisation. Throm. Haemost. 80:624-631.
Reding, M. T., et al. (2000) Sensitization of CD4+ T Cells to Coagulation Factor VIII: Response in Congenital and Acquired Hemophilia Patients and in Healthy Subjects. Thromb. Haemost. 84:643-652.
Reisner, H. M., et al. (1995) Immunogentics of the human immune response to factor VIII. Aledort, L. M., et al., eds. Inhibitors to Coagulation Factors. New York, NY: Plenum Press pp. 65-78.
Saenko, E. L., et al. (1999) Role of Activation of the Coagulation Factor VIII in Interaction with vWf, Phospholipid, and Functioning within the Factor Xase Complex. TCM 9:185-192.
Scandella, D. H. (2000) Properties of Anti-Factor VIII Inhibitor Antibodies in Hemophilia A Patients. Semin. Thromb. Haemost. 26(2):137-142.

(Continued)

*Primary Examiner* — Michael Szperka
(74) *Attorney, Agent, or Firm* — Knobbe Martens Olson & Bear LLP

(57) ABSTRACT

Antigenic fragments of human Factor VIII polypeptide, pharmaceutical compositions which contain these fragments, and complexes containing these peptides and a carrier protein or peptide.

54 Claims, 5 Drawing Sheets

OTHER PUBLICATIONS

Shima, M., et al. (1991) Epitope localization of monoclonal antibodies against factor VIII light chain which inhibit complex formation by factor VIII with von Williebrand factor. Intl. J. Haematol. 54:515-522.

Toole, J. J., et al. (1984) Molecular cloning of a cDNA encoding human antihaemophilic factor. Nature 312:342-347.

Tuddenham, E. G. D. and McVey, J. H. (1998) The genetic basis of inhibitor development in haemophilia A. Haemophilia 4:543-545.

Van Den Brink, E. N., et al. (2000) Human antibodies with specificity for the C2 domain of factor VIII are derived from VH1 germline genes. Blood. 95(2):558-563.

Van Regenmortel, M. H. V. (1996) Mapping Epitope Structure and Activity: From One-Dimensional Prediction to Four-Dimensional Description of Antigenic Specificity. Methods: A Companion to Methods in Enzymology 9:465-472.

Vehar, G. A., et al. (1984) Structure of human factor VIII. Nature 312:337-342.

Vermylen, J. (1998) How do some haemophiliacs develop inhibitors? Hemophilia 4:538-542.

Nogami et al., Anticoagulant effects of a synthetic peptide containing residues Thr-22S3-Gln-2270 within factor VIII C2 domain that selectively inhibits factor Xa-catalysed factor VIII activation, British Journal of Haematology, vol. 116, pp. 868-874, 2002.

Nishiya et al., Anticoagulant Effect of a Synthetic Peptide Containing Residues THR2253-GLN2270 Within Factor VIII C2 Domain Which Selectively Inhibits Factor Xa-Catalyzed Factor VIII Activation, Blood, vol. 96, p. 632a, Nov. 16, 2000.

Nogami et al., Role of Factor VIII C2 Domain in Factor VIII Binding to Factor Xa, J. Biol. Chem. 274, pp. 31000-31007, Oct. 22, 1999.

Villard et al., Low Molecular Weight Peptides Restore the Procoagulant Activity of Factor VIII in the Presence of the Potent Inhibitor Antibody ESH8, The Journal of Biological Chemistry, vol. 277, No. 30, pp. 27232-27239, 2002.

Di Giambattista et al., Mapping of Natural Anti-Factor VIII Antibodies in Plasma Pools from Healthy Donors: Use of Rationally Designed Synthetic Peptides, Biologicals, vol. 29, pp. 229-232, 2001.

Di Giambattista et al., In silico prediction of FVIII epitopes recognised by natural autoantibodies in polyvalent immunoglobulin concentrates, Molecular Immunology, vol. 44, pp. 1903-1913, 2007.

Eaton et al, Construction and Characterization of an Active Factor VIII Variant Lacking the Central One-Third of the Molecule, Biochemistry, vol. 25, No. 26, pp. 8343-8347, 1986.

Foster et al, A Synthetic Factor VIII Peptide of Eight Amino Acid Residues (1677-1684) Contains the Binding Region of an Anti-Factor VIII Antibody which Inhibits the Binding of Factor VIII to von Willebrand Factor, Thrombosis and Haemostasis, vol. 63, pp. 403-406, 1990.

Jones et al, 2005, Identification and removal of a promiscuous CD4+ T cell epitope from the C1 domain of factor VIII, Journal of Thrombosis and Haemostasis, vol. 3, pp. 991-1000.

Lubahn et al., Identification of a F.VIII epitope recognized by a human hemophilic inhibitor, Blood, vol. 73, No. 2, pp. 497-499, 1989.

Muelien et al., A new recombinant procoagulant protein derived from the cDNA encoding human factor VIII, Protein Engineering, vol. 2, No. 4, pp. 301-306, 1988.

Reding et al., Epitope repertoire of human CD4[+] T cells on the A3 domain of coagulation factor VIII, Journal of Thrombosis and Haemostasis, vol. 2, pp. 1385-1394, 2004.

Shima et al., Common inhibitory effects of human anti-C2 domain inhibitor alloantibodies on factor VIII binding to von Willebrand factor., British Journal of Haematology, 1995, 91, pp. 714-721.

Lewis et al., Phospholipid vesicles interfere with the binding of antibody fragments to the light chain of factor VIII, Thromb Haemost 2005; 93: 833-41.

Saenko et al., Slowed Release of Thrombin-cleaved Factor VIII from von Willebrand Factor by a Monoclonal and a Human Antibody Is a Novel Mechanism for Factor VIII Inhibition, Journal of Biological Chemistry, vol. 271, No. 44, Nov. 1, pp. 27424-27431, 1996.

Scandella et al., Epitope mapping of human factor VIII inhibitor antibodies by deletion analysis of factor VIII fragments expressed in *Escherichia coli*, Proc. Natl. Acad. Sci. USA, vol. 85, pp. 6152-6156, Aug. 1988.

Scott et al., Mutagenesis lowers factor VIII immunogenicity, Blood, Aug. 1, 2004, vol. 104, No. 3, pp. 598-599.

Shima et al., A factor VIII neutralizing monoclonal antibody and a human inhibitor alloantoody recognizing in the C2 domain inhibit factor VIII binfing to von Willebrand factor and to phosphatidylserine, Thromb Haemost. Mar. 1, 1993;69(3):240-6 (abstract).

* cited by examiner

SEQUENCE LISTING

```
<160> NUMBER OF SEQ ID NOS: 49

<210> SEQ ID NO 1
<211> LENGTH: 17
<212> TYPE: PRT
<213> ORGANISM: Homo sapiens
<220> FEATURE:
<223> OTHER INFORMATION: epitope Arg 1648 to Tyr 1664 of A3 domain of
      Factor VIII

<400> SEQUENCE: 1

Arg Asp Ile Thr Arg Thr Thr Leu Gln Ser Asp Gln Glu Glu Ile Asp
 1               5                  10                  15

Tyr

<210> SEQ ID NO 2
<211> LENGTH: 16
<212> TYPE: PRT
<213> ORGANISM: Homo sapiens
<220> FEATURE:
<223> OTHER INFORMATION: epitope Asp 1681 to Arg 1696 of A3 domain of
      Factor VIII

<400> SEQUENCE: 2

Asp Glu Asp Glu Asn Gln Ser Pro Arg Ser Phe Gln Lys Lys Thr Arg
 1               5                  10                  15

<210> SEQ ID NO 3
<211> LENGTH: 10
<212> TYPE: PRT
<213> ORGANISM: Homo sapiens
<220> FEATURE:
<223> OTHER INFORMATION: epitope Thr 1739 to Tyr 1748 of A3 domain of
      Factor VIII

<400> SEQUENCE: 3

Thr Asp Gly Ser Phe Thr Gln Pro Leu Tyr
 1               5                  10

<210> SEQ ID NO 4
<211> LENGTH: 9
<212> TYPE: PRT
<213> ORGANISM: Homo sapiens
<220> FEATURE:
<223> OTHER INFORMATION: epitope Asn 1777 to Phe 1785 of A3 domain of
      Factor VIII

<400> SEQUENCE: 4

Asn Gln Ala Ser Arg Pro Tyr Ser Phe
 1               5

<210> SEQ ID NO 5
<211> LENGTH: 22
<212> TYPE: PRT
<213> ORGANISM: Homo sapiens
<220> FEATURE:
<223> OTHER INFORMATION: epitope Glu 1794 to Tyr 1815 of A3 domain of
      Factor VIII

<400> SEQUENCE: 5

Glu Asp Gln Arg Gln Gly Ala Glu Pro Arg Lys Asn Phe Val Lys Pro
```

```
                1               5                  10                  15
Asn Glu Thr Lys Thr Tyr
            20

<210> SEQ ID NO 6
<211> LENGTH: 9
<212> TYPE: PRT
<213> ORGANISM: Homo sapiens
<220> FEATURE:
<223> OTHER INFORMATION: epitope Met 1823 to Asp 1831 of A3 domain of
      Factor VIII

<400> SEQUENCE: 6

Met Ala Pro Thr Lys Asp Glu Phe Asp
1               5

<210> SEQ ID NO 7
<211> LENGTH: 7
<212> TYPE: PRT
<213> ORGANISM: Homo sapiens
<220> FEATURE:
<223> OTHER INFORMATION: epitope Glu 1885 to Phe 1891 of A3 domain of
      Factor VIII

<400> SEQUENCE: 7

Glu Thr Lys Ser Trp Tyr Phe
1               5

<210> SEQ ID NO 8
<211> LENGTH: 16
<212> TYPE: PRT
<213> ORGANISM: Homo sapiens
<220> FEATURE:
<223> OTHER INFORMATION: epitope Glu 1885 to Ala 1901 of A3 domain of
      Factor VIII

<400> SEQUENCE: 8

Glu Thr Lys Ser Trp Phe Thr Glu Asn Met Glu Arg Asn Cys Arg Ala
1               5                   10                  15

<210> SEQ ID NO 9
<211> LENGTH: 9
<212> TYPE: PRT
<213> ORGANISM: Homo sapiens
<220> FEATURE:
<223> OTHER INFORMATION: epitope Asp 1909 to Arg 1917 of A3 domain of
      Factor VIII

<400> SEQUENCE: 9

Asp Pro Thr Phe Lys Glu Asn Tyr Arg
1               5

<210> SEQ ID NO 10
<211> LENGTH: 14
<212> TYPE: PRT
<213> ORGANISM: Homo sapiens
<220> FEATURE:
<223> OTHER INFORMATION: epitope Ser 2018 to His 2031 of A3 domain of
      Factor VIII

<400> SEQUENCE: 10

Ser Asn Lys Cys Gln Thr Pro Leu Gly Met Ala Ser Gly His
1               5                   10

<210> SEQ ID NO 11
<211> LENGTH: 21
<212> TYPE: PRT
<213> ORGANISM: Homo sapiens
```

```
<220> FEATURE:
<223> OTHER INFORMATION: epitope Ala 108 to Val 128 of A1 domain of
      Factor VIII

<400> SEQUENCE: 11

Ala Ser Glu Gly Ala Glu Tyr Asp Asp Gln Thr Ser Gln Arg Glu Lys
 1               5                  10                  15

Glu Asp Asp Lys Val
             20

<210> SEQ ID NO 12
<211> LENGTH: 12
<212> TYPE: PRT
<213> ORGANISM: Homo sapiens
<220> FEATURE:
<223> OTHER INFORMATION: epitope Glu 181 to Leu 192 of A1 domain of
      Factor VIII

<400> SEQUENCE: 12

Glu Gly Ser Leu Ala Lys Glu Lys Thr Gln Thr Leu
 1               5                  10

<210> SEQ ID NO 13
<211> LENGTH: 25
<212> TYPE: PRT
<213> ORGANISM: Homo sapiens
<220> FEATURE:
<223> OTHER INFORMATION: epitope Asp 203 to Ala 227 of A1 domain of
      Factor VIII

<400> SEQUENCE: 13

Asp Glu Gly Lys Ser Trp His Ser Glu Thr Lys Asn Ser Leu Met Gln
 1               5                  10                  15

Asp Arg Asp Ala Ala Ser Ala Arg Ala
             20                  25

<210> SEQ ID NO 14
<211> LENGTH: 29
<212> TYPE: PRT
<213> ORGANISM: Homo sapiens
<220> FEATURE:
<223> OTHER INFORMATION: epitope Asp 327 to Met 355 of A1 domain of
      Factor VIII

<400> SEQUENCE: 14

Asp Ser Cys Pro Glu Glu Pro Gln Leu Arg Met Lys Asn Asn Glu Glu
 1               5                  10                  15

Ala Glu Asp Tyr Asp Asp Asp Leu Thr Asp Ser Glu Met
             20                  25

<210> SEQ ID NO 15
<211> LENGTH: 23
<212> TYPE: PRT
<213> ORGANISM: Homo sapiens
<220> FEATURE:
<223> OTHER INFORMATION: epitope Asp 403 to Lys 425 of A2 domain of
      Factor VIII

<400> SEQUENCE: 15

Asp Asp Arg Ser Tyr Lys Ser Gln Tyr Leu Asn Asn Gly Pro Gln Arg
 1               5                  10                  15

Ile Gly Arg Lys Tyr Lys Lys
             20

<210> SEQ ID NO 16
<211> LENGTH: 11
```

```
<212> TYPE: PRT
<213> ORGANISM: Homo sapiens
<220> FEATURE:
<223> OTHER INFORMATION: epitope Val 517 to Arg 527 of A2 domain of
      Factor VIII

<400> SEQUENCE: 16

Val Glu Asp Gly Pro Thr Lys Ser Asp Pro Arg
 1               5                  10

<210> SEQ ID NO 17
<211> LENGTH: 11
<212> TYPE: PRT
<213> ORGANISM: Homo sapiens
<220> FEATURE:
<223> OTHER INFORMATION: epitope Tyr 555 to Gln 565 of A2 domain of
      Factor VIII

<400> SEQUENCE: 17

Tyr Lys Glu Ser Val Asp Gly Arg Gly Asn Gln
 1               5                  10

<210> SEQ ID NO 18
<211> LENGTH: 9
<212> TYPE: PRT
<213> ORGANISM: Homo sapiens
<220> FEATURE:
<223> OTHER INFORMATION: epitope His 693 to Gly 701 of A2 domain of
      Factor VIII

<400> SEQUENCE: 18

His Asn Ser Asp Phe Arg Asn Arg Gly
 1               5

<210> SEQ ID NO 19
<211> LENGTH: 16
<212> TYPE: PRT
<213> ORGANISM: Homo sapiens
<220> FEATURE:
<223> OTHER INFORMATION: epitope Ser 710 to Asp 725 of A2 domain of
      Factor VIII

<400> SEQUENCE: 19

Ser Cys Asp Lys Asn Thr Gly Asp Tyr Tyr Gly Asp Ser Tyr Glu Asp
 1               5                  10                  15

<210> SEQ ID NO 20
<211> LENGTH: 12
<212> TYPE: PRT
<213> ORGANISM: Homo sapiens
<220> FEATURE:
<223> OTHER INFORMATION: epitope Leu 730 to Ser 741 of A2 domain of
      Factor VIII

<400> SEQUENCE: 20

Leu Leu Ser Lys Asn Asn Ala Ile Glu Pro Arg Ser
 1               5                  10

<210> SEQ ID NO 21
<211> LENGTH: 13
<212> TYPE: PRT
<213> ORGANISM: Homo sapiens
<220> FEATURE:
<223> OTHER INFORMATION: epitope Ser 817 to Ser 830 of A2 domain of
      Factor VIII

<400> SEQUENCE: 21

Ser Asp Asp Pro Ser Gly Ala Ile Asp Ser Asn Asn Ser
 1               5                  10
```

```
<210> SEQ ID NO 22
<211> LENGTH: 15
<212> TYPE: PRT
<213> ORGANISM: Homo sapiens
<220> FEATURE:
<223> OTHER INFORMATION: epitope Ile 2081 to Ser 2095 of C domain of
      Factor VIII

<400> SEQUENCE: 22

Ile His Gly Ile Lys Thr Gln Gly Ala Arg Gln Lys Phe Ser Ser
1               5                   10                  15

<210> SEQ ID NO 23
<211> LENGTH: 17
<212> TYPE: PRT
<213> ORGANISM: Homo sapiens
<220> FEATURE:
<223> OTHER INFORMATION: epitope Tyr 2105 to Gly 2121 of C domain of
      Factor VIII

<400> SEQUENCE: 23

Tyr Ser Leu Asp Gly Lys Lys Trp Gln Thr Tyr Arg Gly Asn Ser Thr
1               5                   10                  15
Gly

<210> SEQ ID NO 24
<211> LENGTH: 10
<212> TYPE: PRT
<213> ORGANISM: Homo sapiens
<220> FEATURE:
<223> OTHER INFORMATION: epitope Asn 2128 to Asn 2138 of C domain of
      Factor VIII

<400> SEQUENCE: 24

Asn Val Asp Ser Ser Gly Ile Lys His Asn
1               5                   10

<210> SEQ ID NO 25
<211> LENGTH: 12
<212> TYPE: PRT
<213> ORGANISM: Homo sapiens
<220> FEATURE:
<223> OTHER INFORMATION: epitope His 2152 to Arg 2163 of C domain of
      Factor VIII

<400> SEQUENCE: 25

His Pro Thr His Tyr Ser Ile Arg Ser Thr Leu Arg
1               5                   10

<210> SEQ ID NO 26
<211> LENGTH: 17
<212> TYPE: PRT
<213> ORGANISM: Homo sapiens
<220> FEATURE:
<223> OTHER INFORMATION: epitope Ser 2181 to Asn 2198 of C domain of
      Factor VIII

<400> SEQUENCE: 26

Ser Lys Ala Ile Ser Asp Ala Gln Ile Thr Ala Ser Ser Tyr Phe Thr
1               5                   10                  15
Asn

<210> SEQ ID NO 27
<211> LENGTH: 19
<212> TYPE: PRT
<213> ORGANISM: Homo sapiens
```

-continued

```
<220> FEATURE:
<223> OTHER INFORMATION: epitope Ser 2204 to Gln 2222 of C domain of
      Factor VIII

<400> SEQUENCE: 27

Ser Pro Ser Lys Ala Arg Leu His Leu Gln Gly Arg Ser Asn Ala Trp
1               5                   10                  15

Arg Pro Gln

<210> SEQ ID NO 28
<211> LENGTH: 17
<212> TYPE: PRT
<213> ORGANISM: Homo sapiens
<220> FEATURE:
<223> OTHER INFORMATION: epitope Gln 2235 to Leu 2251 of C domain of
      Factor VIII

<400> SEQUENCE: 28

Gln Lys Thr Met Lys Val Thr Gly Val Thr Thr Gln Gly Val Lys Ser
1               5                   10                  15

Leu

<210> SEQ ID NO 29
<211> LENGTH: 10
<212> TYPE: PRT
<213> ORGANISM: Homo sapiens
<220> FEATURE:
<223> OTHER INFORMATION: epitope Gly 2242 to Leu 2251 of C domain of
      Factor VIII

<400> SEQUENCE: 29

Gly Val Thr Thr Gln Gly Val Lys Ser Leu
1               5                   10

<210> SEQ ID NO 30
<211> LENGTH: 9
<212> TYPE: PRT
<213> ORGANISM: Homo sapiens
<220> FEATURE:
<223> OTHER INFORMATION: epitope Ile 2262 to Gln 2270 of C domain of
      Factor VIII

<400> SEQUENCE: 30

Ile Ser Ser Ser Gln Asp Gly His Gln
1               5

<210> SEQ ID NO 31
<211> LENGTH: 17
<212> TYPE: PRT
<213> ORGANISM: Homo sapiens
<220> FEATURE:
<223> OTHER INFORMATION: epitope Leu 2273 to Ser 2289 of C domain of
      Factor VIII

<400> SEQUENCE: 31

Leu Phe Phe Gln Asn Gly Lys Val Lys Val Phe Gln Gly Asn Gln Asp
1               5                   10                  15

Ser

<210> SEQ ID NO 32
<211> LENGTH: 14
<212> TYPE: PRT
<213> ORGANISM: Homo sapiens
<220> FEATURE:
<223> OTHER INFORMATION: epitope Pro 2292 to Tyr 2305 of C domain of
      Factor VIII
```

```
<400> SEQUENCE: 32

Pro Val Val Asn Ser Leu Asp Pro Pro Leu Leu Thr Arg Tyr
1               5                   10

<210> SEQ ID NO 33
<211> LENGTH: 11
<212> TYPE: PRT
<213> ORGANISM: Homo sapiens
<220> FEATURE:
<223> OTHER INFORMATION: epitope Glu 2322 to Tyr 2332 of C domain of
      Factor VIII

<400> SEQUENCE: 33

Glu Val Leu Gly Cys Glu Ala Gln Asp Leu Tyr
1               5                   10

<210> SEQ ID NO 34
<211> LENGTH: 4
<212> TYPE: PRT
<213> ORGANISM: Homo sapiens

<400> SEQUENCE: 34

Arg Asp Ile Thr
1

<210> SEQ ID NO 35
<211> LENGTH: 4
<212> TYPE: PRT
<213> ORGANISM: Homo sapiens

<400> SEQUENCE: 35

Asp Glu Asp Glu
1

<210> SEQ ID NO 36
<211> LENGTH: 4
<212> TYPE: PRT
<213> ORGANISM: Homo sapiens

<400> SEQUENCE: 36

Pro Tyr Ser Phe
1

<210> SEQ ID NO 37
<211> LENGTH: 3
<212> TYPE: PRT
<213> ORGANISM: Homo sapiens

<400> SEQUENCE: 37

Glu Asp Gln
1

<210> SEQ ID NO 38
<211> LENGTH: 9
<212> TYPE: PRT
<213> ORGANISM: Homo sapiens

<400> SEQUENCE: 38

Glu Asp Gln Arg Gln Gly Ala Glu Pro
1               5

<210> SEQ ID NO 39
<211> LENGTH: 7
<212> TYPE: PRT
<213> ORGANISM: Homo sapiens
```

```
<400> SEQUENCE: 39

Gly Thr Lys Ser Trp Phe Thr
1               5

<210> SEQ ID NO 40
<211> LENGTH: 3
<212> TYPE: PRT
<213> ORGANISM: Homo sapiens

<400> SEQUENCE: 40

Cys Arg Ala
1

<210> SEQ ID NO 41
<211> LENGTH: 9
<212> TYPE: PRT
<213> ORGANISM: Homo sapiens

<400> SEQUENCE: 41

Asp Arg Asp Ala Ala Ser Ala Arg Ala
1               5

<210> SEQ ID NO 42
<211> LENGTH: 8
<212> TYPE: PRT
<213> ORGANISM: Homo sapiens

<400> SEQUENCE: 42

Asp Asp Leu Thr Asp Ser Glu Met
1               5

<210> SEQ ID NO 43
<211> LENGTH: 4
<212> TYPE: PRT
<213> ORGANISM: Homo sapiens

<400> SEQUENCE: 43

Asp Asp Arg Ser
1

<210> SEQ ID NO 44
<211> LENGTH: 4
<212> TYPE: PRT
<213> ORGANISM: Homo sapiens

<400> SEQUENCE: 44

Ile His Gly Ile
1

<210> SEQ ID NO 45
<211> LENGTH: 3
<212> TYPE: PRT
<213> ORGANISM: Homo sapiens

<400> SEQUENCE: 45

Tyr Ser Leu
1

<210> SEQ ID NO 46
<211> LENGTH: 3
<212> TYPE: PRT
<213> ORGANISM: Homo sapiens

<400> SEQUENCE: 46

Phe Thr Asn
```

<210> SEQ ID NO 47
<211> LENGTH: 4
<212> TYPE: PRT
<213> ORGANISM: Homo sapiens

<400> SEQUENCE: 47

Val Lys Ser Leu
 1

<210> SEQ ID NO 48
<211> LENGTH: 3
<212> TYPE: PRT
<213> ORGANISM: Homo sapiens

<400> SEQUENCE: 48

Thr Arg Tyr
 1

<210> SEQ ID NO 49
<211> LENGTH: 2351
<212> TYPE: PRT
<213> ORGANISM: Homo sapiens
<220> FEATURE:
<221> NAME/KEY: SIGNAL
<222> LOCATION: (1)...(19)

<400> SEQUENCE: 49

Met Gln Ile Glu Leu Ser Thr Cys Phe Phe Leu Cys Leu Leu Arg Phe
                -15                 -10                  -5

Cys Phe Ser Ala Thr Arg Arg Tyr Tyr Leu Gly Ala Val Glu Leu Ser
                  1               5                  10

Trp Asp Tyr Met Gln Ser Asp Leu Gly Glu Leu Pro Val Asp Ala Arg
         15                  20                  25

Phe Pro Pro Arg Val Pro Lys Ser Phe Pro Phe Asn Thr Ser Val Val
 30                  35                  40                  45

Tyr Lys Lys Thr Leu Phe Val Glu Phe Thr Asp His Leu Phe Asn Ile
                 50                  55                  60

Ala Lys Pro Arg Pro Pro Trp Met Gly Leu Leu Gly Pro Thr Ile Gln
                 65                  70                  75

Ala Glu Val Tyr Asp Thr Val Val Ile Thr Leu Lys Asn Met Ala Ser
                 80                  85                  90

His Pro Val Ser Leu His Ala Val Gly Val Ser Tyr Trp Lys Ala Ser
                 95                 100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
                145                 150                 155

Tyr Leu Ser His Val Asp Leu Val Lys Asp Leu Asn Ser Gly Leu Ile
                160                 165                 170

Gly Ala Leu Leu Val Cys Arg Glu Gly Ser Leu Ala Lys Glu Lys Thr
                175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                210                 215                 220

-continued

Ala Ala Ser Ala Arg Ala Trp Pro Lys Met His Thr Val Asn Gly Tyr
            225                 230                 235

Val Asn Arg Ser Leu Pro Gly Leu Ile Gly Cys His Arg Lys Ser Val
            240                 245                 250

Tyr Trp His Val Ile Gly Met Gly Thr Thr Pro Glu Val His Ser Ile
            255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
            290                 295                 300

Asp Leu Gly Gln Phe Leu Leu Phe Cys His Ile Ser His Gln His
            305                 310                 315

Asp Gly Met Glu Ala Tyr Val Lys Val Asp Ser Cys Pro Glu Glu Pro
            320                 325                 330

Gln Leu Arg Met Lys Asn Asn Glu Ala Glu Asp Tyr Asp Asp Asp
            335                 340                 345

Leu Thr Asp Ser Glu Met Asp Val Val Arg Phe Asp Asp Asn Ser
350                 355                 360                 365

Pro Ser Phe Ile Gln Ile Arg Ser Val Ala Lys Lys His Pro Lys Thr
            370                 375                 380

Trp Val His Tyr Ile Ala Ala Glu Glu Asp Trp Asp Tyr Ala Pro
            385                 390                 395

Leu Val Leu Ala Pro Asp Asp Arg Ser Tyr Lys Ser Gln Tyr Leu Asn
            400                 405                 410

Asn Gly Pro Gln Arg Ile Gly Arg Lys Tyr Lys Val Arg Phe Met
            415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
            450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Arg Leu Pro Lys
            480                 485                 490

Gly Val Lys His Leu Lys Asp Phe Pro Ile Leu Pro Gly Glu Ile Phe
            495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
            530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Ile Met Ser Asp Lys Arg Asn Val
            560                 565                 570

Ile Leu Phe Ser Val Phe Asp Glu Asn Arg Ser Trp Tyr Leu Thr Glu
            575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
            610                 615                 620

Phe Asp Ser Leu Gln Leu Ser Val Cys Leu His Glu Val Ala Tyr Trp
            625                 630                 635

Tyr Ile Leu Ser Ile Gly Ala Gln Thr Asp Phe Leu Ser Val Phe Phe
            640                 645                 650

-continued

```
Ser Gly Tyr Thr Phe Lys His Lys Met Val Tyr Glu Asp Thr Leu Thr
        655             660             665
Leu Phe Pro Phe Ser Gly Glu Thr Val Phe Met Ser Met Glu Asn Pro
670             675             680             685
Gly Leu Trp Ile Leu Gly Cys His Asn Ser Asp Phe Arg Asn Arg Gly
                690             695             700
Met Thr Ala Leu Leu Lys Val Ser Ser Cys Asp Lys Asn Thr Gly Asp
            705             710             715
Tyr Tyr Glu Asp Ser Tyr Glu Asp Ile Ser Ala Tyr Leu Leu Ser Lys
        720             725             730
Asn Asn Ala Ile Glu Pro Arg Ser Phe Ser Gln Asn Ser Arg His Pro
    735             740             745
Ser Thr Arg Gln Lys Gln Phe Asn Ala Thr Thr Ile Pro Glu Asn Asp
750             755             760             765
Ile Glu Lys Thr Asp Pro Trp Phe Ala His Arg Thr Pro Met Pro Lys
            770             775             780
Ile Gln Asn Val Ser Ser Ser Asp Leu Leu Met Leu Leu Arg Gln Ser
        785             790             795
Pro Thr Pro His Gly Leu Ser Leu Ser Asp Leu Gln Glu Ala Lys Tyr
    800             805             810
Glu Thr Phe Ser Asp Asp Pro Ser Pro Gly Ala Ile Asp Ser Asn Asn
815             820             825
Ser Leu Ser Glu Met Thr His Phe Arg Pro Gln Leu His His Ser Gly
830             835             840             845
Asp Met Val Phe Thr Pro Glu Ser Gly Leu Gln Leu Arg Leu Asn Glu
            850             855             860
Lys Leu Gly Thr Thr Ala Ala Thr Glu Leu Lys Lys Leu Asp Phe Lys
        865             870             875
Val Ser Ser Thr Ser Asn Asn Leu Ile Ser Thr Ile Pro Ser Asp Asn
    880             885             890
Leu Ala Ala Gly Thr Asp Asn Thr Ser Ser Leu Gly Pro Pro Ser Met
895             900             905
Pro Val His Tyr Asp Ser Gln Leu Asp Thr Thr Leu Phe Gly Lys Lys
910             915             920             925
Ser Ser Pro Leu Thr Glu Ser Gly Gly Pro Leu Ser Leu Ser Glu Glu
            930             935             940
Asn Asn Asp Ser Lys Leu Leu Glu Ser Gly Leu Met Asn Ser Gln Glu
        945             950             955
Ser Ser Trp Gly Lys Asn Val Ser Ser Thr Glu Ser Gly Arg Leu Phe
    960             965             970
Lys Gly Lys Arg Ala His Gly Pro Ala Leu Leu Thr Lys Asp Asn Ala
975             980             985
Leu Phe Lys Val Ser Ile Ser Leu Leu Lys Thr Asn Lys Thr Ser Asn
990             995             1000            1005
Asn Ser Ala Thr Asn Arg Lys Thr His Ile Asp Gly Pro Ser Leu Leu
            1010            1015            1020
Ile Glu Asn Ser Pro Ser Val Trp Gln Asn Ile Leu Glu Ser Asp Thr
        1025            1030            1035
Glu Phe Lys Lys Val Thr Pro Leu Ile His Asp Arg Met Leu Met Asp
    1040            1045            1050
Lys Asn Ala Thr Ala Leu Arg Leu Asn His Met Ser Asn Lys Thr Thr
1055            1060            1065
Ser Ser Lys Asn Met Glu Met Val Gln Gln Lys Lys Glu Gly Pro Ile
```

```
            1070            1075            1080            1085
Pro Pro Asp Ala Gln Asn Pro Asp Met Ser Phe Phe Lys Met Leu Phe
                1090            1095            1100

Leu Pro Glu Ser Ala Arg Trp Ile Gln Arg Thr His Gly Lys Asn Ser
                1105            1110            1115

Leu Asn Ser Gly Gln Gly Pro Ser Pro Lys Gln Leu Val Ser Leu Gly
                1120            1125            1130

Pro Glu Lys Ser Val Glu Gly Gln Asn Phe Leu Ser Glu Lys Asn Lys
                1135            1140            1145

Val Val Val Gly Lys Gly Glu Phe Thr Lys Asp Val Gly Leu Lys Glu
1150            1155            1160            1165

Met Val Phe Pro Ser Ser Arg Asn Leu Phe Leu Thr Asn Leu Asp Asn
                1170            1175            1180

Leu His Glu Asn Asn Thr His Asn Gln Glu Lys Lys Ile Gln Glu Glu
                1185            1190            1195

Ile Glu Lys Lys Glu Thr Leu Ile Gln Glu Asn Val Val Leu Pro Gln
                1200            1205            1210

Ile His Thr Val Thr Gly Thr Lys Asn Phe Met Lys Asn Leu Phe Leu
                1215            1220            1225

Leu Ser Thr Arg Gln Asn Val Glu Gly Ser Tyr Asp Gly Ala Tyr Ala
1230            1235            1240            1245

Pro Val Leu Gln Asp Phe Arg Ser Leu Asn Asp Ser Thr Asn Arg Thr
                1250            1255            1260

Lys Lys His Thr Ala His Phe Ser Lys Lys Gly Glu Glu Asn Leu
                1265            1270            1275

Glu Gly Leu Gly Asn Gln Thr Lys Gln Ile Val Glu Lys Tyr Ala Cys
                1280            1285            1290

Thr Thr Arg Ile Ser Pro Asn Thr Ser Gln Gln Asn Phe Val Thr Gln
                1295            1300            1305

Arg Ser Lys Arg Ala Leu Lys Gln Phe Arg Leu Pro Leu Glu Glu Thr
                1310            1315            1320            1325

Glu Leu Glu Lys Arg Ile Ile Val Asp Asp Thr Ser Thr Gln Trp Ser
                1330            1335            1340

Lys Asn Met Lys His Leu Thr Pro Ser Thr Leu Thr Gln Ile Asp Tyr
                1345            1350            1355

Asn Glu Lys Glu Lys Gly Ala Ile Thr Gln Ser Pro Leu Ser Asp Cys
                1360            1365            1370

Leu Thr Arg Ser His Ser Ile Pro Gln Ala Asn Arg Ser Pro Leu Pro
                1375            1380            1385

Ile Ala Lys Val Ser Ser Phe Pro Ser Ile Arg Pro Ile Tyr Leu Thr
1390            1395            1400            1405

Arg Val Leu Phe Gln Asp Asn Ser Ser His Leu Pro Ala Ala Ser Tyr
                1410            1415            1420

Arg Lys Lys Asp Ser Gly Val Gln Glu Ser Ser His Phe Leu Gln Gly
                1425            1430            1435

Ala Lys Lys Asn Asn Leu Ser Leu Ala Ile Leu Thr Leu Glu Met Thr
                1440            1445            1450

Gly Asp Gln Arg Glu Val Gly Ser Leu Gly Thr Ser Ala Thr Asn Ser
                1455            1460            1465

Val Thr Tyr Lys Lys Val Glu Asn Thr Val Leu Pro Lys Pro Asp Leu
1470            1475            1480            1485

Pro Lys Thr Ser Gly Lys Val Glu Leu Leu Pro Lys Val His Ile Tyr
                1490            1495            1500
```

```
Gln Lys Asp Leu Phe Pro Thr Glu Thr Ser Asn Gly Ser Pro Gly His
        1505                1510                1515

Leu Asp Leu Val Glu Gly Ser Leu Leu Gln Gly Thr Glu Gly Ala Ile
        1520                1525                1530

Lys Trp Asn Glu Ala Asn Arg Pro Gly Lys Val Pro Phe Leu Arg Val
        1535                1540                1545

Ala Thr Glu Ser Ser Ala Lys Thr Pro Ser Lys Leu Leu Asp Pro Leu
1550                1555                1560                1565

Ala Trp Asp Asn His Tyr Gly Thr Gln Ile Pro Lys Glu Glu Trp Lys
                1570                1575                1580

Ser Gln Glu Lys Ser Pro Glu Lys Thr Ala Phe Lys Lys Asp Thr
        1585                1590                1595

Ile Leu Ser Leu Asn Ala Cys Glu Ser Asn His Ala Ile Ala Ala Ile
        1600                1605                1610

Asn Glu Gly Gln Asn Lys Pro Glu Ile Glu Val Thr Trp Ala Lys Gln
        1615                1620                1625

Gly Arg Thr Glu Arg Leu Cys Ser Gln Asn Pro Val Leu Lys Arg
1630                1635                1640                1645

His Gln Arg Glu Ile Thr Arg Thr Thr Leu Gln Ser Asp Gln Glu Glu
                1650                1655                1660

Ile Asp Tyr Asp Asp Thr Ile Ser Val Glu Met Lys Lys Glu Asp Phe
            1665                1670                1675

Asp Ile Tyr Asp Glu Asp Glu Asn Gln Ser Pro Arg Ser Phe Gln Lys
            1680                1685                1690

Lys Thr Arg His Tyr Phe Ile Ala Ala Val Glu Arg Leu Trp Asp Tyr
        1695                1700                1705

Gly Met Ser Ser Ser Pro His Val Leu Arg Asn Arg Ala Gln Ser Gly
1710                1715                1720                1725

Ser Val Pro Gln Phe Lys Lys Val Val Phe Gln Glu Phe Thr Asp Gly
                1730                1735                1740

Ser Phe Thr Gln Pro Leu Tyr Arg Gly Glu Leu Asn Glu His Leu Gly
        1745                1750                1755

Leu Leu Gly Pro Tyr Ile Arg Ala Glu Val Glu Asp Asn Ile Met Val
        1760                1765                1770

Thr Phe Arg Asn Gln Ala Ser Arg Pro Tyr Ser Phe Tyr Ser Ser Leu
1775                1780                1785

Ile Ser Tyr Glu Glu Asp Gln Arg Gln Gly Ala Glu Pro Arg Lys Asn
1790                1795                1800                1805

Phe Val Lys Pro Asn Glu Thr Lys Thr Tyr Phe Trp Lys Val Gln His
        1810                1815                1820

His Met Ala Pro Thr Lys Asp Glu Phe Asp Cys Lys Ala Trp Ala Tyr
        1825                1830                1835

Phe Ser Asp Val Asp Leu Glu Lys Asp Val His Ser Gly Leu Ile Gly
        1840                1845                1850

Pro Leu Leu Val Cys His Thr Asn Thr Leu Asn Pro Ala His Gly Arg
        1855                1860                1865

Gln Val Thr Val Gln Glu Phe Ala Leu Phe Phe Thr Ile Phe Asp Glu
1870                1875                1880                1885

Thr Lys Ser Trp Tyr Phe Thr Glu Asn Met Glu Arg Asn Cys Arg Ala
                1890                1895                1900

Pro Cys Asn Ile Gln Met Glu Asp Pro Thr Phe Lys Glu Asn Tyr Arg
        1905                1910                1915

Phe His Ala Ile Asn Gly Tyr Ile Met Asp Thr Leu Pro Gly Leu Val
        1920                1925                1930
```

```
Met Ala Gln Asp Gln Arg Ile Arg Trp Tyr Leu Leu Ser Met Gly Ser
    1935                1940                1945

Asn Glu Asn Ile His Ser Ile His Phe Ser Gly His Val Phe Thr Val
1950                1955                1960                1965

Arg Lys Lys Glu Glu Tyr Lys Met Ala Leu Tyr Asn Leu Tyr Pro Gly
                1970                1975                1980

Val Phe Glu Thr Val Glu Met Leu Pro Ser Lys Ala Gly Ile Trp Arg
            1985                1990                1995

Val Glu Cys Leu Ile Gly Glu His Leu His Ala Gly Met Ser Thr Leu
            2000                2005                2010

Phe Leu Val Tyr Ser Asn Lys Cys Gln Thr Pro Leu Gly Met Ala Ser
            2015                2020                2025

Gly His Ile Arg Asp Phe Gln Ile Thr Ala Ser Gly Gln Tyr Gly Gln
2030                2035                2040                2045

Trp Ala Pro Lys Leu Ala Arg Leu His Tyr Ser Gly Ser Ile Asn Ala
                2050                2055                2060

Trp Ser Thr Lys Glu Pro Phe Ser Trp Ile Lys Val Asp Leu Leu Ala
                2065                2070                2075

Pro Met Ile Ile His Gly Ile Lys Thr Gln Gly Ala Arg Gln Lys Phe
            2080                2085                2090

Ser Ser Leu Tyr Ile Ser Gln Phe Ile Ile Met Tyr Ser Leu Asp Gly
            2095                2100                2105

Lys Lys Trp Gln Thr Tyr Arg Gly Asn Ser Thr Gly Thr Leu Met Val
2110                2115                2120                2125

Phe Phe Gly Asn Val Asp Ser Ser Gly Ile Lys His Asn Ile Phe Asn
                2130                2135                2140

Pro Pro Ile Ile Ala Arg Tyr Ile Arg Leu His Pro Thr His Tyr Ser
                2145                2150                2155

Ile Arg Ser Thr Leu Arg Met Glu Leu Met Gly Cys Asp Leu Asn Ser
            2160                2165                2170

Cys Ser Met Pro Leu Gly Met Glu Ser Lys Ala Ile Ser Asp Ala Gln
    2175                2180                2185

Ile Thr Ala Ser Ser Tyr Phe Thr Asn Met Phe Ala Thr Trp Ser Pro
2190                2195                2200                2205

Ser Lys Ala Arg Leu His Leu Gln Gly Arg Ser Asn Ala Trp Arg Pro
            2210                2215                2220

Gln Val Asn Asn Pro Lys Glu Trp Leu Gln Val Asp Phe Gln Lys Thr
            2225                2230                2235

Met Lys Val Thr Gly Val Thr Thr Gln Gly Val Lys Ser Leu Leu Thr
            2240                2245                2250

Ser Met Tyr Val Lys Glu Phe Leu Ile Ser Ser Ser Gln Asp Gly His
    2255                2260                2265

Gln Trp Thr Leu Phe Phe Gln Asn Gly Lys Val Lys Val Phe Gln Gly
2270                2275                2280                2285

Asn Gln Asp Ser Phe Thr Pro Val Val Asn Ser Leu Asp Pro Pro Leu
                2290                2295                2300

Leu Thr Arg Tyr Leu Arg Ile His Pro Gln Ser Trp Val His Gln Ile
            2305                2310                2315

Ala Leu Arg Met Glu Val Leu Gly Cys Glu Ala Gln Asp Leu Tyr
            2320                2325                2330
```

ANTIGENIC FRAGMENTS OF HUMAN FACTOR VIII POLYPEPTIDES

CROSS-REFERENCE TO RELATED APPLICATIONS

This application is a Continuation of U.S. application Ser. No. 09/853,080, filed May 9, 2001 now abandoned, which is a Continuation-in-Part of U.S. application Ser. No. 08/765,837, filed Sep. 7, 1999, now U.S. Pat. No. 6,866,848, which was a U.S. National Phase application of PCT/BE95/00068, filed Jul. 14, 1995, which claims priority to Belgian Application BE 9400666, filed Jul. 14, 1994, the disclosures of which are incorporated herein by reference in their entireties.

FIELD OF THE INVENTION

The present invention relates to the antigenic polypeptide sequences of factor VIII, to fragments and epitopes of these sequences and to the major parts of these epitopes, to the inhibitors which are directed against these sequences, its fragments, its epitopes and/or major parts of these epitopes, and to anti-inhibitors which are directed against the said inhibitors.

The present invention also relates to a pharmaceutical composition and to a diagnostic device comprising at least one of the above mentioned molecules.

BACKGROUND OF THE INVENTION

FVIII is a large multi-domain protein of 2,332 amino acids made up of three structural domains, A, B and C which are arranged in the order A1:a1:A2:a2:B:a3:A3:C1:C2. The A domains possess more than 40% homology and are also homologous to ceruloplasmin (for recent review, see Pratt (2000) and Saenko (1999)). 30% homology also exists between the A domains of factor V and FVIII. The C domain occurs twice and is reported to be able to bind glyco-conjugates and phospholipids having a net negative charge. It exhibits homology with lectins which are able to bind to negatively charged phospholipids. The platelet attachment site has been located in this region (C2 domain) (Foster et al., (1990)).

These antigenic determinants consist of fragments 351-365 (A1 domain—heavy chain), 713-740 (A2 domain), 1670-1684 (A3 domain—light chain) ($NH_2$ end of the light chain) or else 2303-2332 (C2 domain—light chain) (Foster C, (1990)), fragments 701-750, 1663-1689, 330-472, 1694-1782 (EP-0 202 853), 322-740 and 2170-2322.

The U.S. Pat. No. 5,744,446 describes a hybrid human/animal Factor VIII having a sequence of amino acids selected from the group of the A2 domain fragments 373-540, 373-508, 445-508, 484-508, 404-508, 489-508 and 484-489, with corresponding sequences of porcine or murine Factor VIII, said hybrid being used for the treatment of Factor VIII deficiencies.

The antibodies which recognize these various sites interfere, with the activation of FVIII, the binding of vWf, FIXa, FXa, APC or phospholipids. The specific antibody response to FVIII varies considerably among individuals, and epitopes for inhibitor antibodies have to be determined for all FVIII domains (see for recent review Scandella, 2000; Lollar, 2000).

Other antibodies, which do not inhibit standard activity tests in vitro, can exert an influence on the behavior of FVIII with the other constituents of the coagulation cascade while attaching themselves to sites in the molecule which are at a substantial distance from the active sites. These antibodies can interfere with the natural state of folding of FVIII by altering some of its properties.

Emergence of alloantibodies (inhibitors) that neutralize infused FVIII activity may seriously complicate FVIII replacement therapy. Reported inhibitor incidence rates in hemophiliacs vary considerably. They range around 6-35% (Vermylen et al, 1998). Candidates for genetic predispositions such as large deletions and intron 22 inversion have been found associated with a high incidence of inhibitors and genes that are involved in the immune response as genes MHC class I and class II (Tuddenham and McVey, 1998). Repeat switching from one FVIII product to another and the possibility that some FVIII concentrates are more immunogenic may also explain the appearance of inhibitors (Vermylen et al, 1998). Different methods of preparing FVIII could exert an influence on its structure, its physicochemical properties or its natural microenvironment; Laub et al. (1999); Raut et al. (1998)). Clinically relevant anti-FVIII autoantibodies are rare in non-hemophilic patients (annual frequency in the population: $1-5/10^6$) (Morrisson and Ludlam) (1995). They are associated with a number of autoimmune diseases and are often characterized by life-threatening hemorrhage. On the other hand, anti-FVIII antibodies have also been described in healthy subjects (Algiman et al, 1992; Moreau et al, 2000), without any apparent effect on the subjects' levels of circulating FVIII.

Self proteins or derived peptides may elicit an immune response if presented to CD4 T cells at inflammatory sites by professional antigen presenting cells. Using pools of overlapping synthetic peptides spanning the sequences of individual FVIII domains, Reding et al. (2000) showed reactive $CD4^+$ to FVIII in healthy subjects and hemophilia patients. Several FVIII domains were recognized: A3 domain was recognized more strongly and frequently and each domain forms several epitopes.

Techniques such as western blotting, immunoprecipitation, and enzyme-linked immunosorbent assays (ELISAs), using well-defined FVIII proteolytic fragments, a large recombinant peptide library, or synthetic peptide arrays, have been used to map different FVIII-inhibitor binding sites located mainly in the A2 and C2 domains. However, none of these techniques has made it possible to build a model for identification of inhibitor and non-inhibitor epitopes. Only a few epitopes have been mapped to discrete sequences (<20 amino-acid residues). To solve this problem, Palmer et al (1997) synthesized 96 undecamer peptides (11 amino-acid residues) representing 80% of the complete residue sequence of FVIII. They succeeded in determining the epitope specificity of 9 patients' inhibitory antibodies. Other useful techniques are analysis of FVIII gene mutations and their effects on the FVIII molecule as well as phage display technology (van den Brink et al, 2000). All these methodologies, however, are time consuming, rather costly, and largely dependent on patient availability. Certain areas of the FVIII molecule may be "hot spots" containing commonly recognized clusters of inhibitor epitopes, e.g., regions in the A2 domain, A3 domain, and C2 domain. The reason for these "hot spots" in generating an inhibitor response remains poorly understood (Reisner et al, 1995).

Currently, a predominant notion among hemophilic patients, clinicians and "fractionators" is that of having available a purified FVIII which is devoid of all pathogenic plasma contaminants and secondary effects.

Different animal models could be used as hemophilia dogs, SCID mice, hemophilia mice . . . but until now, no satisfactory experimental model exists which makes it possible to forecast the immunogenicity or the immuno-modulatory effect of the FVIII preparations, or the susceptibility of the host, before they have been administered clinically.

Patients who develop an anti-FVIII immune response find themselves in a serious situation which necessitates the use of severe, aggressive and excessively expensive measures.

One of the frequently treatment, is the induction of immune tolerance by administration of very high doses of FVIII (150 IU/kg twice a day) in association or not with prothrombin complex concentrates and is assigned as "Bonn Protocol". Treatment options are also to by-pass the FVIII inhibitor activity by use of PCC (preferably an activated PCC [APCC]) or FVIIa. Specific antibodies as consequence of the infusion of these alternative agents could be produced, impairing the treatment. As an alternative agent porcine FVIII may be used to achieve hemostasis in patients with antibodies that do not substantially cross-react with porcine FVIII before or during the treatment (Lollar, 2000).

A potential alternative approach to inhibit the production of inhibitors is blockade of the T cell/B cell collaboration mediated by through receptor ligand binding signal events (Ewenstein et al, 2000). Preliminary clinical trials were performed using a humanized mouse monoclonal antibody to human T cell CD40 ligand (CD 154).

A profitable strategy for reducing the level of inhibitors has consisted in subjecting patients to an extracorporeal circulation to enable solid-phase absorption of the total IgG.

The immunoabsorbant could be Sepharose-bound staphylococcal protein A or Sepharose-bound polyclonal sheep antibodies to total human immunoglobulin (Knobf and Derfler, 1999). The foreign proteins (protein A, sheep anti-human Ig) could leak from the column and triggered the immune system of the recipient; moreover problems could raise as sanitization (ICH Topic Q5A, Directive 92/79/EC).

The infusion of polyvalent intravenous immunoglobulins (IVIG), where appropriate combined with an immunosuppressive treatment, has been found to be relatively effective, although the reason for this effectiveness is still not fully established. Various hypotheses involving feed-back inhibition of IgG synthesis, stimulation of IgG clearance or activation of T suppressor cells have been advanced. An interesting explanation is that these commercial intravenous immunoglobulins might contain antibodies which are able to react with the variable parts (idiotypes) of the anti-FVIII antibodies and neutralize these antibodies (Dietrich et al. (1992)).

Unfortunately, none of these approaches has been found to be satisfactory in terms of safety, efficacy, efficiency and cost.

The state of the art in epitope structure prediction was limited given to the fact that non-continuous amino acid residues seem to constitute most important epitope and that the dynamics of binding is often not integrated into the epitope prediction equation making epitope structure prediction a complex four-dimensional problem (Van Regenmortel, Methods: A companion to Methods in Enzymology, 9, page 465-472, 1996).

According to the author, most of the antibodies raised against intact proteins do not react with any peptide fragment derived from the parent protein indicating that such antibodies are directed to discontinuous epitopes (conformational epitopes).

This author states also that low success rate of antigenic prediction is due to the fact that predictions concerns only continuous epitopes and it is unrealistic to reduce the complexity of epitopes that always possess conformational features to one dimensional linear peptide model.

Similarly, Palmer et al. (1997) using synthetic peptide arrays to identify novel Factor VIII inhibitor epitopes note that each patient pattern of anti-factor VIII antibody reactivity appears to be polyclonal, directed against multiple sites located within the amino and carboxyl terminus of the protein and seems to be unique for each plasma investigated (see also above).

Moreover, this author notes that it is difficult to predict the importance that any given antibody: epitope interaction may have on Factor VIII coagulation activity based on the results of synthetic peptide assays alone (due to the incomplete understanding of the relationship between structure and function of different factor VIII domains and the possibility that both inhibitor and non-inhibitory antibodies may be present in a patient's plasma.

Therefore, the documents of the state of the art do not suggest to identify antigenic linear peptides upon a macromolecule (such as Factor VIII) and that linear epitopes could be used for the diagnostic and/or the therapy of immune disorders induced by inhibitors directed against Factor VIII.

The present invention aims to obtain antigenic polypeptide sequences of factor VIII, fragments and epitopes of these sequences, whose purpose is to improve the diagnosis and/or therapy (including prevention) of immune disorders (in particular those induced by inhibitors of FVIII and inhibitors of FVIII, especially inhibitors of the binding of the von Willebrand factor (vWf), to the FIX and/or to membrane phospholipids (PL)), and which allows a screening between non-inhibitory and inhibitory anti-FVIII allo- or auto-antibodies (allo- or auto-immunoglobulins).

Another aim of the invention is to obtain inhibitors which exhibit an immunoaffinity with these antigenic polypeptide sequences, fragments and/or epitopes, as well as to obtain anti-inhibitors, in particular antibodies or (T) cell receptors, which are directed against the above-mentioned said inhibitors and whose purpose is to improve the diagnosis and/or therapy (or prevention) of immune disorders.

A further aim of the invention is to obtain said molecules at high purity, in industrial level, without contaminants (viruses, prions, . . . ) and according to the GMP practices in the field of therapy and diagnostics (ICH topic QSA, Directive 92/79/EC, etc.).

SUMMARY OF THE INVENTION

Some embodiments of the present invention are described in the following numbered paragraphs.

Paragraph 1: An antigenic polypeptide sequence, which is the polypeptide sequence of factor VIII.

Paragraph 2: An antigenic polypeptide sequence, which lacks the following fragments: alanine 322-serine 750, leucine 1655-arginine 1689, lysine 1694-proline 1782 and possibly the fragment aspartic acid 2170-tyrosine 2332.

Paragraph 3: The sequence according to paragraph 1 or 2, which is immunogenic.

Paragraph 4: The sequence according to paragraph 3, which exhibits an immunoaffinity for the receptors of T and/or B lymphocytes.

Paragraph 5: An antigenic fragment of the sequence according to paragraph 1 or 2, which is selected from the group consisting of the polypeptide sequences A1, A2, A3 or C of factor VIII.

Paragraph 6: The antigenic fragment of the polypeptide sequence A3 according to paragraph 5, which is selected from the group consisting of the sequence fragment arginine 1649 to arginine 2031 inclusive, the sequence fragment threonine 1739 to aspartic acid 1831 inclusive and/or the sequence fragment arginine 1803 to arginine 1917 inclusive.

Paragraph 7: A sequence epitope of the fragment according to paragraph 6, which is selected from the group consisting of:

the epitope arginine 1648 to tyrosine 1664 inclusive, defined by the following sequence: SEQ ID NO: 1: Arg Asp Ile Thr Arg Thr Thr Leu Gln Ser Asp Gln Glu Glu Ile Asp Tyr, possibly deleted from one or more amino acids of the tetrapeptide Arg-Asp-Ile-Thr (SEQ ID NO: 34) or one or two of the last amino acids of the peptide Asp-Tyr, the epitope aspartic acid 1681 to arginine 1696 inclusive, defined by the following sequence: SEQ ID NO: 2: Asp Glu Asp Glu Asn Gln Ser Pro Arg Ser Phe Gln Lys Lys Thr Arg, possibly deleted from one or more amino acids of the epitope Asp-Glu-Asp-Glu (SEQ ID NO: 35), the epitope threonine 1739 to tyrosine 1748 inclusive, defined by the following sequence: SEQ ID NO: 3: Thr Asp Gly Ser Phe Thr Gln Pro Leu Tyr, the epitope asparagine 1777 to phenylalanine 1785 inclusive, defined by the following sequence: SEQ ID NO: 4: Asn Gln Ala Ser Arg Pro Tyr Ser Phe, possibly deleted from one or two amino acids of the terminal dipeptide Ser-Phe or the tetrapeptide Pro-Tyr-Ser-Phe (SEQ ID NO: 36), the epitope glutamic acid 1794 to tyrosine 1815 inclusive, defined by the following sequence: SEQ ID NO: 5: Glu Asp Gln Arg Gln Gly Ala Glu Pro Arg Lys Asn Phe Val Lys Pro Asn Glu Thr Lys Thr Tyr, possibly deleted from one or more amino acids from the first tripeptide Glu-Asp-Gln (SEQ ID NO: 37) or the first nonapeptide Glu-Asp-Gln-Arg-Gln-Gly-Ala-Glu-Pro (SEQ ID NO: 38), the epitope methionine 1823 to aspartic acid 1831, defined by the following sequence: SEQ ID NO: 6: Met Ala Pro Thr Lys Asp Glu Phe Asp, the epitope glutamic acid 1885 to phenylalanine 1891 inclusive, defined by the following sequence: SEQ ID NO: 7: Glu Thr Lys Ser Trp Tyr Phe, the epitope glutamic acid 1885 to alanine 1901 inclusive, defined by the following sequence: SEQ ID NO: 8: Gly Thr Lys Ser Trp Phe Thr Glu Asn Met Glu Arg Asn Cys Arg Ala, possibly deleted from one or more amino acids from the heptapeptide Gly-Thr-Lys-Ser-Trp-Phe-Thr (SEQ ID NO: 39) or from the tripeptide Cys-Arg-Ala (SEQ ID NO: 40), the epitope aspartic acid 1909 to arginine 1917 inclusive, defined by the following sequence: SEQ ID NO: 9: Asp Pro Thr Phe Lys Glu Asn Tyr Arg, and the epitope comprised between serine 2018 and histidine 2031 inclusive, defined by the following sequence: SEQ ID NO: 10: Ser Asn Lys Cys Gln Thr Pro Leu Gly Met Ala Ser Gly His.

Paragraph 8: An antigenic fragment of the polypeptide sequence A1 according to paragraph 5, which is alanine 108 to methionine 355 inclusive, preferably alanine 108 to alanine 227 inclusive.

Paragraph 9: A sequence epitope of the fragment according to paragraph 8, which is selected from the group consisting of: the epitope alanine 108 to valine 128 inclusive, defined by the following sequence: SEQ ID NO: 11: Ala Ser Glu Gly Ala Glu Tyr Asp Asp Gln Thr Ser Gln Arg Glu Lys Glu Asp Asp Lys Val, possibly deleted from the terminal amino acids alanine and/or valine, the epitope glutamic acid 181 to leucine 192 inclusive, defined by the following sequence: SEQ ID NO: 12: Glu Gly Ser Leu Ala Lys Glu Lys Thr Gln Thr Leu, possibly deleted from one or two amino acids of the terminal dipeptide Thr-Leu, the epitope aspartic acid 203 to alanine 227 inclusive, defined by the following sequence: SEQ ID NO: 13: Asp Glu Gly Lys Ser Trp His Ser Glu Thr Lys Asn Ser Leu Met Gln Asp Arg Asp Ala Ala Ser Ala Arg Ala, possibly deleted from one or more amino acids of the nonapeptide Asp-Arg-Asp-Ala-Ala-Ser-Ala-Arg-Ala (SEQ ID NO: 41), and the epitope aspartic acid 327 to methionine 355 inclusive, defined by the following sequence: SEQ ID NO: 14: Asp Ser Cys Pro Glu Glu Pro Gln Leu Arg Met Lys Asn Asn Glu Glu Ala Glu Asp Tyr Asp Asp Asp Leu Thr Asp Ser Glu Met, possibly deleted from one or more amino acids of the dipeptide Asp-Ser or the octapeptide Asp-Asp-Leu-Thr-Asp-Ser-Glu-Met (SEQ ID NO: 42), Paragraph 10: An antigenic fragment of the antigenic polypeptide sequence A2 according to paragraph 5, which is aspartic acid 403 to aspartic acid 725 inclusive, preferably histidine 693 to aspartic acid 725 inclusive.

Paragraph 11: A sequence epitope of the fragment according to paragraph 10, which is selected from the group consisting of: the epitope aspartic acid 403 to lysine 425 inclusive, defined by the following sequence: SEQ ID NO: 15: Asp Asp Arg Ser Tyr Lys Ser Gln Tyr Leu Asn Asn Gly Pro Gln Arg Ile Gly Arg Lys Tyr Lys Lys, possibly deleted from one or more amino acids of the tetrapeptide Asp-Asp-Arg-Ser (SEQ ID NO: 43), the epitope valine 517 to arginine 527 inclusive, defined by the following sequence: SEQ ID NO: 16: Val Glu Asp Gly Pro Thr Lys Ser Asp Pro Arg, possibly deleted from one or the two amino acids of the dipeptide Pro-Arg, the epitope tyrosine 555 to glutamine 565 inclusive defined by the following sequence: SEQ ID NO: 17: Tyr Lys Glu Ser Val Asp Gly Arg Gly Asn Gln, the epitope histidine 693 to glycine 701 inclusive, defined by the following sequence: SEQ ID NO: 18: His Asn Ser Asp Phe Arg Asn Arg Gly, the epitope serine 710 to aspartic acid 725 inclusive, defined by the following sequence: SEQ ID NO: 19: Ser Cys Asp Lys Asn Thr Gly Asp Tyr Tyr Gly Asp Ser Tyr Glu Asp, the epitope leucine 730 to serine 741 inclusive, defined by the following sequence: SEQ ID NO: 20: Leu Leu Ser Lys Asn Asn Ala Ile Glu Pro Arg Ser, possibly deleted from the terminal amino acid serine and/or the first amino acid leucine, the epitope serine 817 to serine 830 inclusive, defined by the following sequence: SEQ ID NO: 21: Ser Asp Asp Pro Ser Gly Ala Ile Asp Ser Asn Asn Ser.

Paragraph 12: An antigenic fragment of the antigenic polypeptide sequence C according to paragraph 5, which is lysine 2085 to isoleucine 2251 inclusive, or leucine 2273 to tyrosine 2332 inclusive, preferably lysine 2085 to glycine 2121 inclusive or serine 2182 to leucine 2251 inclusive.

Paragraph 13: A sequence epitope of the fragment according to paragraph 12, which is selected from the group consisting of:

the epitope isoleucine 2081 to serine 2095 inclusive, defined by the following sequence: SEQ ID NO: 22: Ile His Gly Ile Lys Thr Gln Gly Ala Arg Gln Lys Phe Ser Ser, possibly deleted from one or more amino acids of the tetrapeptide Ile-His-Gly-Ile (SEQ ID NO: 44), the epitope tyrosine 2105 to glycine 2121 inclusive, defined by the following sequence: SEQ ID NO: 23: Tyr Ser Leu Asp Gly Lys Lys Trp Gln Thr Tyr Arg Gly Asn Ser Thr Gly, possibly deleted from one or more amino acids of the tripeptide Tyr-Ser-Leu (SEQ ID NO: 45), the epitope asparagine acid 2128 to asparagine acid 2138 inclusive, defined by the following sequence: SEQ ID NO: 24: Asn Val Asp Ser Ser Gly Ile Lys His Asn, the epitope histidine 2152 to arginine 2163 inclusive, defined by the following sequence: SEQ ID NO: 25: His Pro Thr His Tyr Ser Ile Arg Ser Thr Leu Arg;

the epitope serine 2181 to asparagine acid 2198 inclusive, defined by the following sequence: SEQ ID NO: 26: Ser Lys Ala Ile Ser Asp Ala Gln Ile Thr Ala Ser Ser Tyr Phe Thr Asn, possibly deleted from one or more amino acids of the first dipeptide Ser-Tyr or one or more amino acids from the terminal tripeptide Phe-Thr-Asn (SEQ ID NO: 46);

the epitope serine 2204 to glutamine 2222 inclusive, defined by the following sequence: SEQ ID NO: 27: Ser Pro Ser Lys Ala Arg Leu His Leu Gln Gly Arg Ser Asn Ala Trp Arg Pro Gln;

the epitope glutamine 2235 to leucine 2251 inclusive, defined by the following sequence: SEQ ID NO: 28: Gln Lys Thr Met Lys Val Thr Gly Val Thr Thr Gln Gly Val Lys Ser Leu, possibly deleted from one or two amino acids of the terminal dipeptide Ser-Leu or one or more amino acids of the tetrapeptide Val-Lys-Ser-Leu (SEQ ID NO: 47);

the epitope glycine 2242 to leucine 2251 inclusive, defined by the following sequence: SEQ ID NO: 29: Gly Val Thr Thr Gln Gly Val Lys Ser Leu, possibly deleted from one or two amino acids of the terminal dipeptide Ser-Leu;

the epitope isoleucine 2262 to glutamine 2270 inclusive, defined by the following sequence: SEQ ID NO: 30: Ile Ser Ser Ser Gln Asp Gly His Gln;

the epitope leucine 2273 to serine 2289 inclusive, defined by the following sequence: SEQ ID NO: 31: Leu Phe Phe Gln Asn Gly Lys Val Lys Val Phe Gln Gly Asn Gln Asp Ser;

the epitope proline 2292 to tyrosine 2305 inclusive, defined by the following sequence: SEQ ID NO: 32: Pro Val Val Asn Ser Leu Asp Pro Pro Leu Leu Thr Arg Tyr, possibly deleted from one or more amino acids of the terminal tripeptide Thr-Arg-Tyr (SEQ ID NO: 48);

the epitope glutamic acid 2322 to tyrosine 2332 inclusive, defined by the following sequence: SEQ ID NO: 33: Glu Val Leu Gly Cys Glu Ala Gln Asp Leu Tyr.

Paragraph 14: A conformational epitope, which contains at least two different epitopes according to any one of the preceding paragraphs 8, 10 and 12.

Paragraph 15: A pool of more than three fragments or epitopes according to any one of the preceding paragraphs 6 to 14.

Paragraph 16: A recombinant factor VIII having an amino acid sequence deleted from one or more of the fragments or the epitopes according to any one of the paragraphs 6 to 14.

Paragraph 17: A complex comprising a carrier protein or a carrier peptide linked to an element which is selected from the group consisting of the fragment and/or the epitope according to any one of the paragraphs 6 to 14.

Paragraph 18: An inhibitor of factor VIII, which exhibits an immunoaffinity with the sequence, the fragment, the epitope, the pool and/or the complex according to any one of the preceding paragraphs.

Paragraph 19: The inhibitor according to paragraph 18, which is an anti-factor VIII antibody or antibody fragment.

Paragraph 20: An anti-inhibitor, which is directed against the inhibitor of factor VIII according to paragraph 18 or 19.

Paragraph 21: The anti-inhibitor according to paragraph 20, which is an anti-anti-factor VIII idiotype antibody or antibody fragment.

Paragraph 22: A pharmaceutical composition, which comprises an adequate pharmaceutical carrier and at least one element selected from the group consisting of the sequence, the fragment, the epitope, the pool, the complex, the recombinant factor VIII or the inhibitor and/or the anti-inhibitor according to any one of the preceding paragraphs.

Paragraph 23: A diagnostic and/or purification device, which comprises at least one element which is selected from the group consisting of the sequence, the fragment, the epitope, the pool, the complex, the inhibitor and/or the anti-inhibitor according to any one of the preceding paragraphs.

Paragraph 24: The device according to paragraph 23, which is a diagnostic kit.

Paragraph 25: The device according to paragraph 23, which is a chromatography column or filter.

Paragraph 26: A method for a therapeutic treatment and/or prevention of an immune disorder in mammal, wherein the pharmaceutical composition according to paragraph 22 is administered to the mammal patient presently or potentially having said immune disorder, in an amount effective to treat and/or prevent said immune disorder.

Paragraph 27: A method for a therapeutic treatment and/or prevention of an immune disorder in a mammal patient, wherein a physiological fluid such as serum obtained from said mammal patient is put into the chromatography column of paragraph 25 in order to allow a binding with the inhibitors of factor VIII present in said serum with the sequence, the fragment, the epitope, the pool and/or the complex according to any one of the preceding paragraphs 1 to 15, wherein the physiological liquid is eluted from said chromatography column and the physiological liquid from which the inhibitors of factor VIII have been removed is reinjected to the patient.

Paragraph 28: The therapeutic treatment and/or prevention method according to paragraph 26 or 27, wherein the immune disorder is induced by an element selected from the group consisting of inhibitors of factor VIII, inhibitors of the binding of factor VIII to the von Willebrand factor, to the factor IX, the factor X and/or to membrane phospholipids.

Paragraph 29: A process for identifying and obtaining inhibitors and/or anti-inhibitors according to paragraph 18 or 19, comprising the steps of:

selecting an element from the group consisting of the sequence, the fragment, the epitope, the pool and/or the complex according to any one of the preceding paragraphs 1 to 15 or 17, attached to a solid support of a chromatography column, passing a physiological fluid from a patient containing inhibitors of factor VIII through said chromatography column, eluting said column, and collecting the fractions containing inhibitors of factor VIII which have exhibited an immunoaffinity with said element.

Paragraph 30: The process according to paragraph 29, further comprising the steps of:

attaching the collected inhibitors of factor VIII upon the solid support of a chromatography column, passing a physiological fluid from a patient containing anti-inhibitors of factor VIII through said chromatography column, eluting said column, and collecting the fractions containing anti-inhibitors of factor VIII which have exhibited an immunoaffinity with said inhibitors of factor VIII.

DETAILED DESCRIPTION OF THE PREFERRED EMBODIMENT

Figure 1:
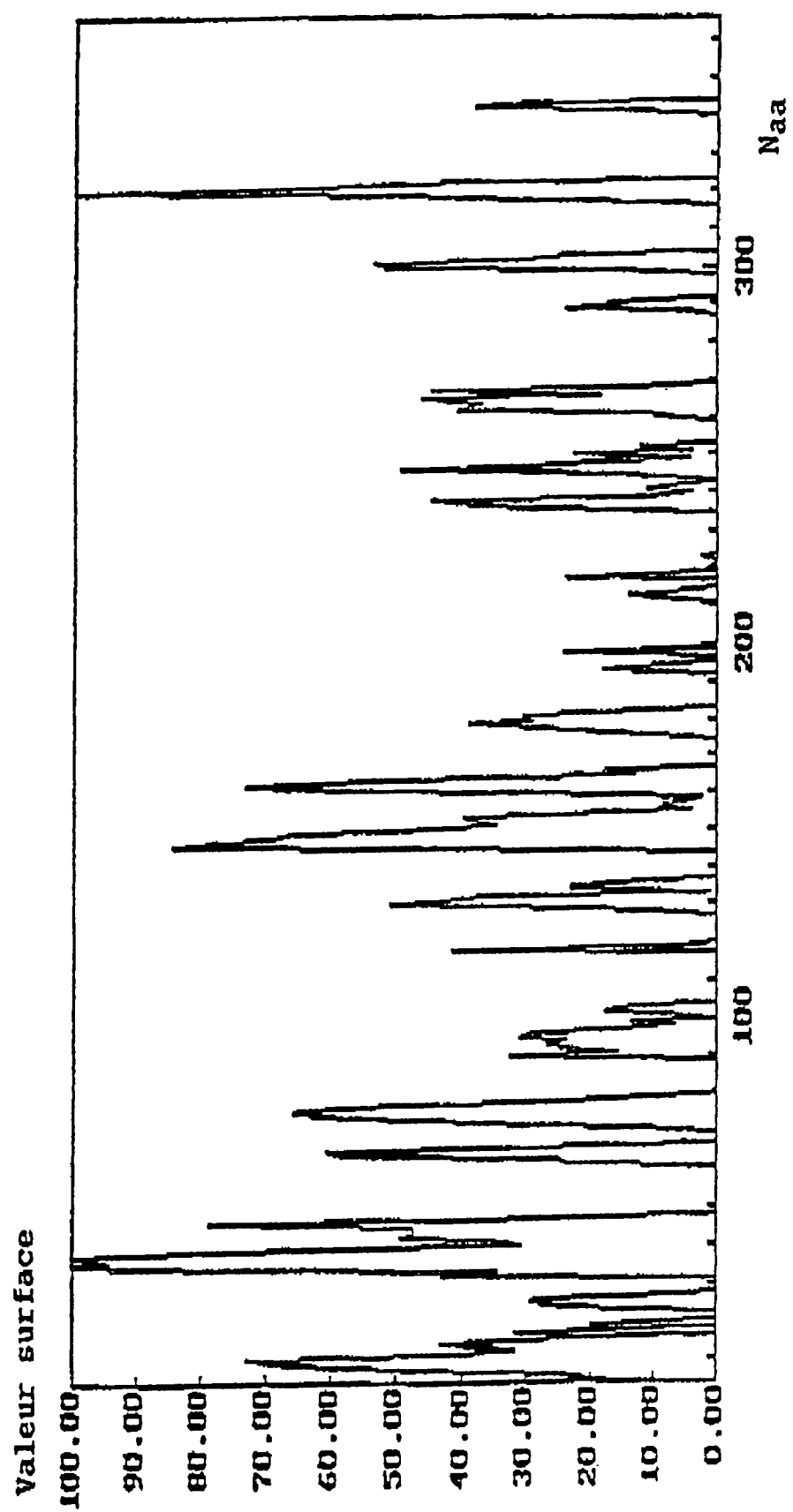
FIG. 1. This figure depicts the hydrophilicity, flexibility and accessibility graph of the A3 sequence of Factor VIII, renumbered 1 to 371 amino acids (surface value for each amino acid).

The present invention relates to the antigenic polypeptide sequences of factor VIII and/or fragments of these sequences, as described by Verhar et al. (1984), the disclosure of which is incorporated herein by reference in its entirety.

The "polypeptide sequence of factor VIII" is understood to be the natural human or animal sequence, which may be glycosylated and which has been obtained by purification from pools of plasma, in particular cryoprecipitate, by synthesis and/or by genetic manipulation (sequence from which portions which are not involved in the mechanism of blood coagulation may have been deleted) of factor VIII.

The present invention relates, in particular, to the antigenic polypeptide sequences of factor VIII which lacks the fragments comprised between alanine 322-serine 750, leucine 1655-arginine 1689 and lysine 1694-proline 1782, and possibly also the fragments comprised between aspartic acid 2170 and tyrosine 2332.

The present invention relates, in particular, to the antigenic polypeptide sequences A1, A2, A3 and C(C1 and C2) of factor VIII.

A first embodiment of the invention relates to the antigenic polypeptide sequence A3 of factor VIII, and to fragments and/or epitopes of this sequence. The said sequence contains the fragments glutamic acid 1649 to histidine 2031 inclusive, arginine 1652 to arginine 1917 inclusive or arginine 1803 to arginine 1917 inclusive, of the polypeptide sequence of factor VIII as published by Verhar et al. (1984) and Toole et al. (1984).

Preferably, the fragments of the said sequence are arginine 1648 to arginine 1696 inclusive, threonine 1739 to aspartic acid 1831 inclusive or glutamic acid 1885 to arginine 1917 inclusive.

The fragments, epitopes and major parts thereof are preferably polypeptidic sequences made of at least 7 amino acids of the FVIII polypeptidic sequence.

The invention also relates to the sequence epitopes of these fragments, in particular:

the epitope arginine 1648 to tyrosine 1664 inclusive, defined by the following sequence: SEQ ID NO: 1: Arg Asp Ile Thr Arg Thr Thr Leu Gln Ser Asp Gln Glu Glu Ile Asp Tyr, and possibly deleted from one or more amino acids of the tetrapeptide Arg-Asp-Ile-Thr (SEQ ID NO: 34) (P7), or one or two of the last amino acids of the dipeptide Asp-Tyr;

the epitope aspartic acid 1681 to arginine 1696 (P8) inclusive, defined by the following sequence: SEQ ID NO: 2: Asp Glu Asp Glu Asn Gln Ser Pro Arg Ser Phe Gln Lys Lys Thr Arg possibly deleted from one or more amino acids of the epitope Asp-Glu-Asp-Glu (SEQ ID NO: 35);

the epitope threonine 1739 to tyrosine 1748 inclusive, defined by the following sequence: SEQ ID NO: 3: Thr Asp Gly Ser Phe Thr Gln Pro Leu Tyr;

the epitope asparagine 1777 to phenylalanine 1785 inclusive, defined by the following sequence: SEQ ID NO: 4: Asn Gln Ala Ser Arg Pro Tyr Ser Phe possibly deleted from one or more amino acids of the terminal dipeptide Ser-Phe or tetrapeptide Pro-Tyr-Ser-Phe (SEQ ID NO: 36);

the epitope glutamic acid 1794 to tyrosine 1815 inclusive, defined by the following sequence: SEQ ID NO: 5: Glu Asp Gln Arg Gln Gly Ala Glu Pro Arg Lys Asn Phe Val Lys Pro Asn Glu Thr Lys Thr Tyr, possibly deleted from one or more amino acids of the first tripeptide Glu-Asp-Gln (SEQ ID NO: 37) (P9) or the first nonapeptide Glu-Asp-Gln-Arg-Gln-Gly-Ala-Glu-Pro (SEQ ID NO: 38);

the epitope methionine 1823 to aspartic acid 1831 inclusive, defined by the following sequence: SEQ ID NO: 6: Met Ala Pro Thr Lys Asp Glu Phe Asp;

the epitope glutamic acid 1885 to phenylalanine 1891 inclusive, defined by the following sequence: SEQ ID NO: 7: Glu Thr Lys Ser Trp Tyr Phe;

the epitope glutamic acid 1885 to alanine 1901 inclusive, defined by the following sequence: SEQ ID NO: 8: Glu Thr Lys Ser Trp Phe Thr Glu Asn Met Glu Arg Asn Cys Arg Ala possibly deleted from one or more amino acids from the heptapeptide Glu-Thr-Lys-Ser-Trp-Phe-Thr (SEQ ID NO: 39) or from the tripeptide Cys-Arg-Ala (SEQ ID NO: 40);

the epitope aspartic acid 1909 to arginine 1917 inclusive, defined by the following sequence: SEQ ID NO: 9: Asp Pro Thr Phe Lys Glu Asn Tyr Arg the epitope comprised between serine 2018 and histidine 2031 inclusive, defined by the following sequence: SEQ ID NO: 10: Ser Asn Lys Cys Gln Thr Pro Leu Gly Met Ala Ser Gly His.

Advantageously, the said sequences, specific fragments and epitopes exhibit an antigenic characteristic which is illustrated by Table 1.

Another preferred embodiment of the invention relates to antigenic polypeptide sequence A1 of factor VIII, fragments and/or epitopes of this sequence.

Preferably, the fragments of the said sequence are alanine 108 to methionine 355 inclusive, preferably alanine 108 to alanine 227 inclusive.

The invention also relates to the sequence epitopes of these fragments, in particular:

the epitope alanine 108 to valine 128 inclusive, defined by the following sequence: SEQ ID NO: 11: Ala Ser Glu Gly Ala Glu Tyr Asp Asp Gln Thr Ser Gln Arg Glu Lys Glu Asp Asp Lys Val possibly deleted from the terminal amino acids alanine and valine (P1);

the epitope glutamic acid 181 to leucine 192 inclusive, defined by the following sequence: SEQ ID NO: 12: Glu Gly Ser Leu Ala Lys Glu Lys Thr Gln Thr Leu possibly deleted from one or two amino acids of the terminal dipeptide Thr-Leu;

the epitope aspartic acid 203 to alanine 227 inclusive, defined by the following sequence: SEQ ID NO: 13: Asp Glu Gly Lys Ser Trp His Ser Glu Thr Lys Asn Ser Leu Met Gln Asp Arg Asp Ala Ala Ser Ala Arg Ala possibly deleted from one or more amino acids of the nonapeptide Asp-Arg-Asp-Ala-Ala-Ser-Ala-Arg-Ala (SEQ ID NO: 41);

the epitope aspartic acid 327 to methionine 355 inclusive, defined by the following sequence: SEQ ID NO: 14: Asp Ser Cys Pro Glu Glu Pro Gln Leu Arg Met Lys Asn Asn Glu Glu Ala Glu Asp Tyr Asp Asp Asp Leu Thr Asp Ser Glu Met possibly deleted from one or more amino acids from the terminal dipeptide Asp-Ser or the octapeptide Asp-Asp-Leu-Thr-Asp-Ser-Glu-Met (SEQ ID NO: 42) (P2).

Another preferred embodiment of the invention relates to the antigenic polypeptide sequence A2 of factor VIII, fragments and/or epitopes of this sequence.

Preferably, the fragments of the said sequence are aspartic acid 403 to serine 840 inclusive, preferably histidine 693 to aspartic acid 725 inclusive.

The invention also relates to the sequence epitopes of these fragments, in particular:

the epitope aspartic acid 403 to lysine 425 inclusive, defined by the following sequence: SEQ ID NO:15: Asp Asp Arg Ser Tyr Lys Ser Gln Tyr Leu Asn Asn Gly Pro Gln Arg Ile Gly Arg Lys Tyr Lys Lys, possibly deleted from one or more amino acids of the tetrapeptide Asp-Asp-Arg-Ser (SEQ ID NO: 43) (P3);

the epitope valine 517 to arginine 527 inclusive, defined by the following sequence: SEQ ID NO: 16: Val Glu Asp Gly Pro Thr Lys Ser Asp Pro Arg possibly deleted from one or the two amino acids of the dipeptide Pro-Arg;

the epitope tyrosine 555 to glutamine 565 inclusive, defined by the following sequence: SEQ ID NO: 17: Tyr Lys Glu Ser Val Asp Gly Arg Gly Asn Gln;

the epitope histidine 693 to glycine 701 inclusive, defined by the following sequence: SEQ ID NO: 18: His Asn Ser Asp Phe Arg Asn Arg Gly;

the epitope serine 710 to aspartic acid 725 inclusive, defined by the following sequence (P4): SEQ ID NO: 19: Ser Cys Asp Lys Asn Thr Gly Asp Tyr Tyr Gly Asp Ser Tyr Glu Asp;

the epitope leucine 730 to serine 741 inclusive, defined by the following sequence (P4): SEQ ID NO: 20: Leu Leu Ser Lys Asn Asn Ala Ile Glu Pro Arg Ser possibly deleted from the terminal amino acid serine (P4) and/or the first amino acid leucine;

the epitope serine 817 to serine 830 inclusive, defined by the following sequence (P5): SEQ ID NO: 21: Ser Asp Asp Pro Ser Gly Ala Ile Asp Ser Asn Asn Ser.

A final preferred embodiment of the invention relates to the antigenic polypeptide sequence C of factor VIII, and fragments and/or epitopes of this sequence. Preferably, the fragments of the said sequence are histidine 2082 to lysine 2251 inclusive or leucine 2273 to tyrosine 2332 inclusive, preferably lysine 2085 to glycine 2121 inclusive and serine 2181 to leucine 2251 inclusive.

The invention also relates to the sequence epitopes of these fragments, in particular:

the epitope isoleucine 2081 to serine 2095 inclusive, defined by the following sequence: SEQ ID NO: 22: Ile His Gly Ile Lys Thr Gln Gly Ala Arg Gln Lys Phe Ser Ser possibly deleted from one or more amino acids from the tetrapeptide Ile-His-Gly-Ile (SEQ ID NO: 44);

the epitope tyrosine 2105 to glycine 2121 inclusive, defined by the following sequence: SEQ ID NO: 23: Tyr Ser Leu Asp Gly Lys Lys Trp Gln Thr Tyr Arg Gly Asn Ser Thr Gly possibly deleted from one or more amino acids of the tripeptide Tyr-Ser-Leu (SEQ ID NO: 45) (P110);

the epitope asparagine 2128 to asparagine 2138 inclusive, defined by the following sequence: SEQ ID NO: 24: Asn Val Asp Ser Ser Gly Ile Lys His Asn;

the epitope histidine 2152 to arginine 2163 inclusive, defined by the following sequence: SEQ ID NO: 25: His Pro Thr His Tyr Ser Ile Arg Ser Thr Leu Arg;

the epitope serine 2181 to asparagine 2198 inclusive, defined by the following sequence: SEQ ID NO: 26: Ser Lys Ala Ile Ser Asp Ala Gln Ile Thr Ala Ser Ser Tyr Phe Thr Asn possibly deleted from one or more amino acids from the terminal tripeptide Phe-Thr-Asn (SEQ ID NO: 46) (P11);

the epitope serine 2204 to glutamine 2222 inclusive, defined by the following sequence (P12): SEQ ID NO: 27: Ser Pro Ser Lys Ala Arg Leu His Leu Gln Gly Arg Ser Asn Ala Trp Arg Pro Gln;

the epitope glutamine 2235 to leucine 2251 inclusive, defined by the following sequence (P13): SEQ ID NO: 28: Gln Lys Thr Met Lys Val Thr Gly Val Thr Thr Gln Gly Val Lys Ser Leu possibly deleted from one or two amino acids of the terminal dipeptide Ser-Leu or one or more amino acids of the tetrapeptide Val-Lys-Ser-Leu (SEQ ID NO: 47);

the epitope glycine 2242 to leucine 2251 inclusive, defined by the following sequence: SEQ ID NO: 29: Gly Val Thr Thr Gln Gly Val Lys Ser Leu possibly deleted from one or two amino acids of the terminal dipeptide Ser-Leu, said epitope presenting a possible partial overlapping with a known monoclonal antibody binding site ESH8 2248-2285;

the epitope isoleucine 2262 to glutamine 2270 inclusive, defined by the following sequence: SEQ ID NO: 30: Ile Ser Ser Ser Gln Asp Gly His Gln;

the epitope leucine 2273 to serine 2289 inclusive, defined by the following sequence (P14): SEQ ID NO: 31: Leu Phe Phe Gln Asn Gly Lys Val Lys Val Phe Gln Gly Asn Gln Asp Ser;

the epitope proline 2292 to tyrosine 2305 inclusive, defined by the following sequence (P15): SEQ ID NO: 32: Pro Val Val Asn Ser Leu Asp Pro Pro Leu Leu Thr Arg Tyr possibly deleted from one or more amino acids of the terminal tripeptide Thr-Arg-Tyr (SEQ ID NO: 48) involved in the phospholipid von Willebrand factor binding site;

the epitope glutamic acid 2322 to tyrosine 2332 inclusive, defined by the following sequence (P116): SEQ ID NO: 33: Glu Val Leu Gly Cys Glu Ala Gln Asp Leu Tyr.

The invention also relates to the major parts of the said epitopes or the said fragments. Said epitopes can be deleted from one or more terminal amino acids, preferably from one, two or three amino acids, or can be replaced by one or more amino acids that present the same characteristic of hydrophilicity, flexibility and accessibility.

It is also known that some of the epitopes according to the invention are comprised in major determinants of human inhibitors epitopes or several factors binding sites or binding sites of known monoclonal antibodies, especially the portion C2 that is known to be the binding site of the monoclonal antibody Mas531P or the binding site ESH8 as well as phospholipids, Factor Xa or the von Willebrand factor binding site. However, the specific epitopes according to the invention or their major parts are preferred selected portions of said binding sites or may include a possible overlapping with said binding sites.

In other cases, the epitopes according to the invention are more specific portions of known epitopes. Therefore, an artificial epitope could be easily obtained by synthesis and the specific above-described fragments can be deleted from non-epitopic portions such as the fragment described in a C2 fragment (amino acids phenylalanine 2196 to tryptophan 2203 inclusive and amino acids valine 2222 to phenylalanine 2234 inclusive, or the sequence leucine 2252 to threonine 2272 inclusive or the amino acids phenylalanine 2290 to threonine 2291 inclusive as well as the amino acids leucine 2306 to methionine 2321 inclusive).

These sequences, these fragments and these epitopes are particularly advantageously characterized by high hydrophilicity, which has been defined by Parker and Hodges (1986), considerable flexibility, which has been defined by Karplus and Schultz (1985) and considerable accessibility, which has been defined by Janin (1979).

These fragments and these epitopes are, in particular, exposed on the surface of the factor VIII protein and exhibit pronounced antigenic and immunogenic characteristics.

Another aspect of the present invention is related to a modified (recombinant or transgenic) FVIII, possibly obtained by genetic engineering, and deleted from one or more of the above-identified fragments, epitopes or major parts of said epitopes and/or said fragments.

Advantageously, said FVIII still allows the binding of coagulation factor(s), but will be less immunogenic and will not induce or induce less the formation of inhibitors directed against said modified FVIII or natural FVIII.

Advantageously, said polypeptide sequences, fragments or epitopes are also independently immunogenic (that is to say they are immunogenic even without being complexed with a protein of large size such as BSA, KLH hemocyanin, etc.), and preferably exhibit an immunoaffinity within inhibitors of factor VIII, such as anti-factor VIII antibodies, and/or exhibit an immunoaffinity for the receptors of the T lymphocytes and possibly B lymphocytes.

These sequences, fragments, epitopes and/or major parts of said fragments or said epitopes induce an immune reaction (antibody synthesis) when they are injected into a rabbit.

These characteristics are particularly pronounced in the case of the epitopes SEQ ID NO: 2 and SEQ ID NO: 5, which comprise sequences which are relatively "long" in amino acids, i.e. comprise 16 and 22 amino acids, respectively.

Said sequences are unexpectedly characterized by substantial immunogenicity towards monoclonal and polyclonal antibodies, but are sufficiently short to be readily and advantageously obtained by synthesis.

The present invention also relates to the conformational epitopes which comprise at least two different fragments of said sequence, at least two sequence epitopes and/or at least two major parts of said epitopes or said different fragments according to the invention and above identified.

The conformational epitopes are made up of two or more different portions of a polypeptide sequence, which portions are located in proximity to each other when the protein is folded in its tertiary or quaternary structure.

These epitopes are capable of being "recognized" (that is to say of exhibiting an immunoaffinity), preferably simultaneously, with inhibitors of factor VIII, in particular B and T lymphocytes (by way of the major histocompatibility locus (MHC I and/or II)) and/or anti-factor VIII antibodies (Scandella et al. (2000); Reding et al. (2000)).

Preferably, the said sequence, said fragments, said epitopes and/or the major parts of said epitopes or said fragments are complexed with a carrier protein or a carrier peptide, such as BSA, or KLH hemocyanin, as to form a complex exhibiting a more powerful immunogenicity.

The present invention is also related to a pool of more than three of said fragments, epitopes or major parts of said epitopes having advantageously important antigenic and/or immunogenic properties and which may be used advantageously in a diagnostic or therapeutic method or device such as a kit or a dialysis column, etc. allowing an efficient, preferably complete, screening and characterization of the major (if not all) known inhibitors directed against factor VIII by (human) patients.

Another aspect of the present invention relates to an inhibitor of factor VIII which exhibits an immunoaffinity with antigenic polypeptide sequences according to the present invention, with fragments and epitopes of said sequences, with the major parts of said epitopes or said fragments and/or with the complex according to the invention.

An inhibitor is understood to mean any biological molecule or cell (such as a T-lymphocyte) binding to said FVIII and capable of giving rise to immune disorders (characterized by humoral immune response and/or cellular immune response against said FVIII).

In particular, such an inhibitor can be an anti-factor VIII monoclonal or polyclonal antibody or antibody fragment (such as the hypervariable Fab portion of the said antibody) which inactivates the said factor VIII and/or which inhibits the binding of factor VIII to the von Willebrand factor and/or to membrane phospholipids.

Advantageously, the said inhibitors are synthesized by a "chimeric" animal which comprises a human immune system, such as a hu-SCID mouse or transgenic mouse producing human antibodies or other antibodies production technologies as phage display technology or immortalized B-cells, by EPV in particular.

Another aspect of the invention relates to an anti-inhibitor which is directed against the said previously described factor VIII inhibitor.

An anti-inhibitor which is directed against the factor VIII inhibitor is understood to mean any chemical or biological molecule, a cell and/or a cell fragment (receptor) which is capable of interfering with the said inhibitor in such a way as to ensure its inactivation or avoid or reduce its binding to the factor VIII.

Preferably, such an anti-inhibitor is an anti-anti-factor VIII idiotype (monoclonal or polyclonal) antibody or antibody fragment, natural or obtained by genetic engineering.

Another aspect of the invention relates to a pharmaceutical composition which comprises an adequate pharmaceutical carrier or a diluent and an element selected from the group consisting of said antigenic polypeptide sequence of factor VIII, fragments and epitopes of this sequence or a pool thereof, an inhibitor of factor VIII which is directed against them, an anti-inhibitor which is directed against the said inhibitor, and/or a mixture of these.

The type and amount of adequate pharmaceutical carrier or diluent (and possibly adjuvant or excipient) present in said pharmaceutical composition, may vary according to the method of administration and is possibly combined an adjuvant in order to improve therapeutical properties of the pharmaceutical composition according to the invention or to reduce its possible side effects. Suitable pharmaceutical acceptable carriers used in the pharmaceutical composition according to the invention are well known by the person skilled in the art and are selected according to the methods generally applied by pharmacists and may include solid, liquid or gaseous non-toxic pharmaceutically acceptable carriers. The percentage of active product/pharmaceutical acceptable carrier may vary within very large ranges only limited by the tolerance and the possible side effects on patients (including humans), and by frequency and/or mode of administration.

Another aspect of the invention relates to a diagnostic and/or purification device, such as a diagnostic kit, an affinity filter, or a chromatography column which comprises an element which is selected from the group consisting of these antigenic polypeptide sequences, fragments and epitopes and/or major parts of said epitopes or said fragments, the complex according to the invention or a pool thereof, an inhibitor which is directed against them, an anti-inhibitor which is directed against said inhibitor, and/or a mixture of these. Advantageously, said device comprises a pool of said epitopes which allow a screening of patients and may detect the most important inhibitors present in said patients and which allow a positive test with enough specificity and sensibility.

The purification device can therefore consist of a chromatography column which comprises these sequences of factor VIII, fragments and epitopes and/or major parts of said fragments or epitopes, attached to the solid phase of the chromatography column.

A physiological liquid (such as serum), which is derived from a patient and which comprises inhibitors of factor VIII pass through this chromatography column, with said inhibitors (for example antibodies) becoming attached specifically to said factor VIII sequences, fragments, epitopes or said major parts or a pool thereof. Following elution, it is possible to collect said inhibitors by causing them to react with anti-inhibitors (anti-anti-factor VIII idiotype antibodies).

It is also possible to characterize the anti-anti-factor VIII idiotype antibodies which are present in a serum by these anti-inhibitors passed through a chromatography column on which inhibitors of factor VIII have been attached to the solid phase.

It is also possible to reinject (ex vivo treatment) the physiological liquid (blood or serum or a derived fraction) to said patient after its inhibitors of factor VIII have been removed by binding with said factor VIII fragments, epitopes or a pool thereof; said inhibitors being removed from the physiological fluid (blood or serum) similarly as proposed for dialysis method applied to human patients.

The present invention is also related to a method of treatment (ex vivo treatment) of a patient suffering from a pathology induced by inhibitors to the factor VIII which comprises the steps of extracting said physiological liquid (blood or serum) from the patient, obtaining its reaction upon a solid support binding the factor VIII fragments, epitopes or a pool thereof according to the invention and reinjecting said physiological liquid to the patient after the removing of the inhibitors having fixed said factor VIII fragments, epitopes, majors parts or a pool thereof.

A final aspect of the invention relates to the use of the pharmaceutical composition according to the invention for preparing a medicament used for preventing and/or treating immune disorders, in particular those induced by inhibitors of factor VIII, inhibitors of the binding of factor VIII to the factor IX and/or the factor X and/or the von Willebrand factor (vWF) and/or inhibitors of the binding of factor VIII to membrane phospholipids.

The present invention will be described in details in the following non-limiting examples in reference to the enclosed figures.

EXAMPLES

Materials and Methods

Reagents: MAS530p (Harlan-Seralab, Indianapolis, Ind.) is a mouse monoclonal antibody specific for the 44-kDa A2 domain of the factor VIII heavy chain. Biotin-labeled rabbit IgG anti-mouse IgG was purchased from Dakopatts (Copenhagen, Denmark). Biotin-labeled goat IgG anti-human IgG and biotin-labeled mouse IgG anti-rabbit IgG were obtained from Sigma Chemicals (St Louis, Mich.), purified α-thrombin (3000 IU/mg), streptavidin-peroxidase conjugate, ovalbumin (OVA), bovine serum albumin (BSA), keyhole limpet hemocyanin (KLH), and o-phenylenediamine (OPD) were purchased from Sigma Chemicals (St. Louis, Mich.). Casein was obtained from Merck (Darmstadt, Germany). 4-chloro-1-naphtol and biotinylated molecular weight markers were obtained from Bio-Rad Laboratories (Hercules, Calif.). Freund's adjuvant was from Difco (Detroit, Mich.).

FVIII concentrates: Plasma FVIII (p-FVIII) was a solvent/detergent-treated FVIII concentrate (100 IU/mg protein) purified by ion exchange chromatography (FVIII Conc. SD, CAF-DCF-Red Cross, Brussels, Belgium). Albumin-free recombinant FVIII (rFVIII) was obtained from Hyland (Glendale, Calif.).

Plasma fraction immunoglobulins: Cohn Fraction II+III was obtained from large plasma pool from 4,800 unpaid donors, after precipitation in the presence of increasing ethanol concentration. This fraction contains all Ig classes and subclasses. IgG composition was determined by nephelometry. The relative percentage of each subclass was 63,7; 30,1; 3,4 and 2,8 for IgG1, IgG2, IgG3 and IgG4 respectively (average values for 3 different batches of FII+III).

Factor VIII Concentrates Factor VIII Activity and Activity Inhibition

Factor VIII activity was determined in a one-stage clotting assay adapted for use on the Coagulometer KC4A (Sigma Diagnostics). The assay uses severe hemophilia A plasma (Organon Teknika, Cambridge, UK) and APPT reagent from Instrumentation Laboratory (Warrington, UK). Potencies were calculated relative to the $5^{th}$ International Standard FVIII concentrate 88/640 (5.4 IU/ml) (NIBSC, Potters Bar, UK). FVIII-inhibitory activity was measured in purified rabbit and human IgG preparations according to the modified Bethesda assay. Briefly, affinity-purified IgGs were serially diluted and incubated for 1 h in the presence of FVIII concentrate 88/640 (1 IU/ml) at 37° C. The residual FVIII activity was measured as described above.

Activation of factor VIII by α-thrombin and immunoblotting has been described elsewhere (Peerlinck et al, 1997).

Synthesis of peptides, conjugation of peptides to carrier proteins and production of rabbit anti-peptide antisera were performed by Neosystem (Strasbourg, France).

Purification of Rabbit and Human Antibodies by Affinity Chromatography

For purification of rabbit and human antibodies, 5 mg of each different peptide was coupled to 1 ml pre-packed NHS-activated Sepharose (Pharmacia Biotech, Uppsala, Sweden) according to the manufacturer's instructions. Specific antipeptide antibodies were purified with an automated liquid chromatography system (ÄKTAexplorer 100A, Pharmacia Uppsala, Sweden) either from 50 ml rabbit antiserum or from 100 ml of a human plasma fraction, obtained after Cohn fractionation (fraction II+III; 13 mg protein/ml). Briefly, samples were dialyzed 3 times against 5 volumes of TE buffer (20 mM Tris-HCl pH 7.2, 150 mM NaCl and 0.02% $NaN_3$) and loaded onto the column at a flow rate of 1 ml/min. The column was sequentially washed at 2 ml/min with 50 ml TE buffer and 30 ml TE containing 1 M NaCl. After absorption, the material was eluted (1 ml/min) with 5 ml of 0.1 M citric acid pH 2.5 and directly recovered in 5 ml of 1M Tris-HCl, pH 9.0. Samples were finally dialyzed versus 10 volumes of equilibration buffer and concentrated on Centriprep-30 (Amicon, Beverly, Mass.). Ig recovery was determined by the Bio-Rad protein assay.

Selection of Potential Factor-VIII Linear Epitopes

More than 30 surface regions (linear epitopes) spanning 8 to 25 residues, characterized by a high hydrophilicity, flexibility and accessibility were identified on the FVIII molecule. On the basis of their high probability of an outer location (see FIG. 1 for A3), 16 linear peptides (P1 to P16) were selected, matching identified stretches of 13 or more amino-acid residues. These peptides were synthesized and coupled to ovalbumin for production of specific antiserum (Table 1, hereafter). P8 includes the epitope described by Shima et al (1988) and was used as an external control.

Experimental Results Obtained from Said Synthesized Linear Epitopes Using the Rabbit Model Results are summarized in Table 1 which concerns the characterization of rabbit anti-FVIII-peptide antisera and recovered affinity-purified of immunoglobulins.

Sixteen synthetic peptides (from 10 to 20 amino acids) were selected in the A, B, C1 and C2 domains. After conjugation with ovalbumin, the OVA-peptide conjugates were injected into rabbits and FVIII anti-peptide antisera RAP1 to RAP16 were studied.

More precisely, two rabbits were immunized with each FVIII-peptide-ovalbumin preparation. Specific antisera RAP1 to RAP16 (column b, Table 1) were prepared and assayed in an ELISA (column c, Table 1) using rFVIII or FVIII-peptide-KLH as the antigen. ELISA titer is expressed as the negative log of the reciprocal of the serum dilution giving 50% binding. The immunoglobulins were then purified by chromatography on peptide-bound Sepharose. The FVIII domain recognized by the anti-FVIII peptide Ig after immunoblotting is shown in (column d, Table 1) and Ig protein recoveries (column e, Table 1) were measured using immunoglobulins as the standard. The inhibitory activity, expressed in BU/mg protein, was determined in a FVIII neutralizing activity assay (column f, Table 1).

Immunogenicity of FVIII Peptides and Characterization of Rabbit Anti-FVIII Peptide Antisera The reactivity of FVIII anti-peptide antisera was measured by an ELISA using, as antigen, either the different corresponding FVIII-peptide coupled to KLH protein or purified rFVIII. The binding reaction of each anti-FVIII-peptide antiserum was specific both for the FVIII peptide used to elicit the immune response in rabbit and for rFVIII (see Table 1).

To demonstrate the FVIII epitope specificity of the rabbit anti-peptide antibodies, rFVIII and the rFVIII fragments obtained after treatment with thrombin were resolved by SDS-PAGE and analyzed by western blotting with the different preparations of rabbit IgGs. As expected, most antisera (14/16, 87%), showed a strong reaction with the corresponding FVIII fragment containing the selected linear epitope (see Table 1).

Purification of Rabbit-anti-FVIII Peptide Antibodies

The specific rabbit IgG were purified by affinity chromatography on peptide-Sepharose as described under Methods. When FVIII-neutralizing activity was measured in a one-stage clotting assay, significant inhibition was found with two rabbit IgG purified preparations: RAP2, corresponding to IgG specific for SEQ ID No. 14 and RAP7 specific for SEQ ID NO: 1.

Epitope Mapping of Rabbit Anti-FVIII Peptide Antibodies by Immunoblotting with Human rFVIII To demonstrate the FVIII epitope specificity of the rabbit anti-peptide antibodies, rFVIII and the rFVIII fragments obtained after treatment with thrombin were resolved by SDS-PAGE and analyzed by western blotting with different preparations of rabbit IgGs (RAP1 to RAP17 Igs).

In each run, the rFVIII heavy chain (HC) and light chain (LC) and their thrombin proteolysis products (44 kDa and 72 kDa) were identified with a mixture of two monoclonal antibodies, MoAb 530p and MoAb18, respectively specific for the heavy and light chain. MoAb18 recognizes the NH$_2$-terminal light-chain FVIII fragment obtained after thrombin activation, which proved too small to remain in the gel after electrophoresis. Fourteen of the 17 rabbit immunoglobulin preparations reacted strongly with both rFVIII and pFVIII. Antisera RAP1, RAP2, RAP3, RAP4 recognized exclusively the heavy chains (200 kDa to 92 kDa). Antisera RAP1 and RAP2 reacted with the 50-kDa A1-domain fragment; RAP3 and RAP4 bound to the 44-kDa fragment (domain A2); RAP5 (specific for the B domain) bound to the high-molecular-weight FVIII heavy chain (about 200-kDa).

RAP7, RAP8, and RAP9 reacted with the 80-kDa light-chain doublet. RAP9 and RAP12 to RAP17 antibodies also detected the 72-kDa FVIII light-chain fragment. As expected, each reactive antiserum showed a strong reaction with the corresponding FVIII fragment containing the selected linear epitope. No reaction was detectable in the gels between RAP6 or RAP10 and the HC or LC FVIII fragments.

Experimental Results Obtained from Said Synthesized Linear Epitopes to Purify and Characterize Human Autoantibodies Table 2 concerns the characterization of human anti-FVIII antibodies from Cohn fraction II+III of healthy individuals.

Human anti-peptide IgG preparations (HAP1 through HAP17) were so far purified on Sepharose coupled to 13 different FVIII peptides (column a, Table 2). The Igs (column b, Table 2) were analyzed by immunoblotting. Binding to the rFVIII HC or LC chains and to the rFVIII thrombin fragment is shown respectively in columns c and d, Table 2. FVIII-domain reactivity is shown in column e, Table 2. Arrows indicate a decrease in 80-kDa band intensity. Ig recovery (column f, Table 2) after affinity purification is expressed in μg/10 mg loaded FII+III (see Materials and Methods). Inhibition of the clotting assay was determined after incubation in the presence of each of the 13 Ig preparations in the Bethesda assay (column g, Table 2).

Figure 2A:
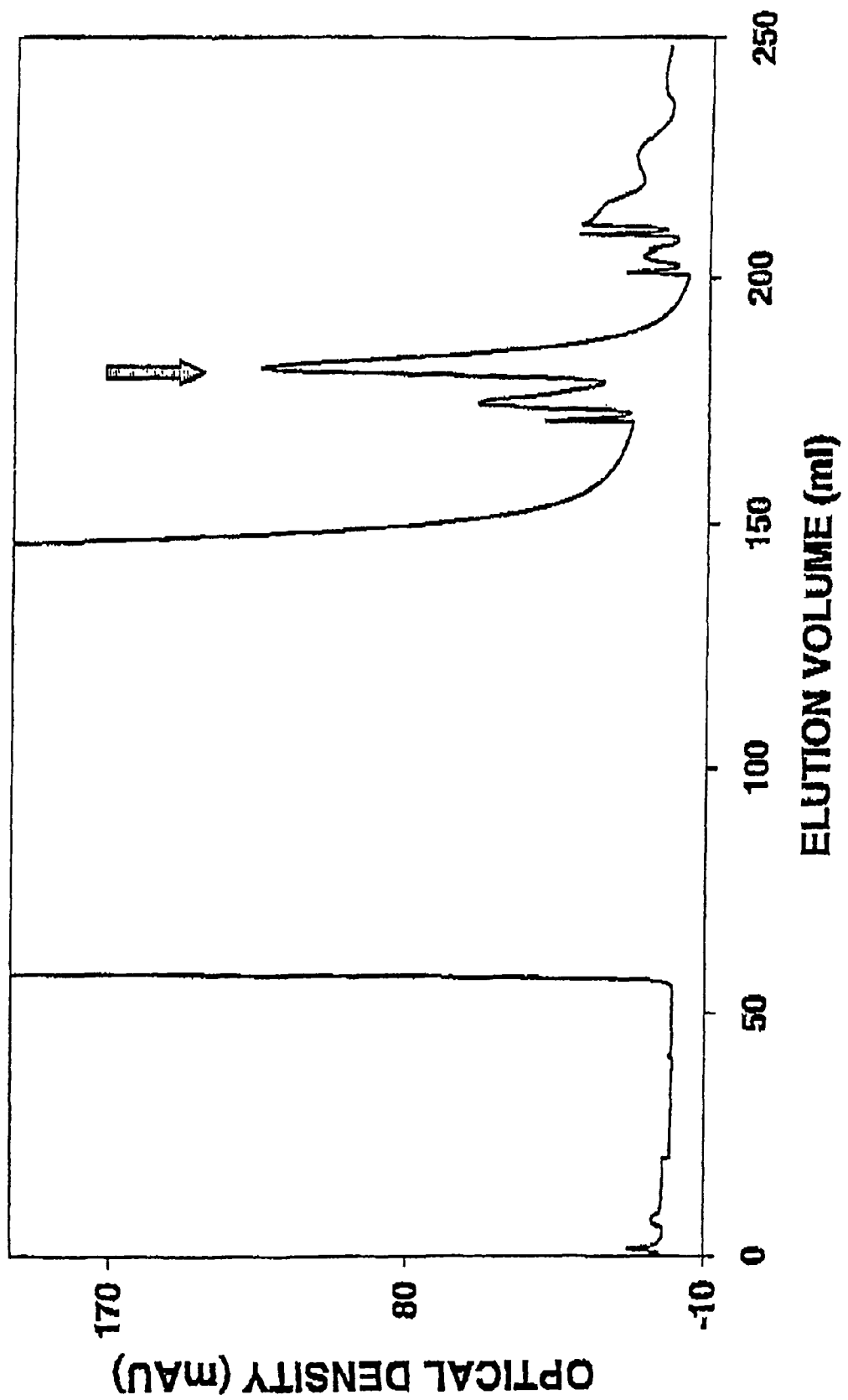
FIG. 2. This FIG. (2a) represents the elution profile related to the purification of human anti-SEQ ID NO: 32 antibodies by affinity chromatography in peptide-Sepharose column. Cohn fraction II+III solution (50 mL) was loaded onto the column (1 mL gel) at a flow rate of 1 mL/min. The separation of specific antibodies was performed as described in the Examples. The arrow indicates the position of specific human anti-SEQ ID NO: 32. IgG purified from Cohn fraction II+III. The clotting activity of FVIII (2b) was measured as described in Examples in the presence of increasing amount of anti-SEQ ID NO: 32. The of FVIII activity=(FVIII activity in the presence of antibody/FVIII activity in the absence of antibody)*100.
Figure 2B:
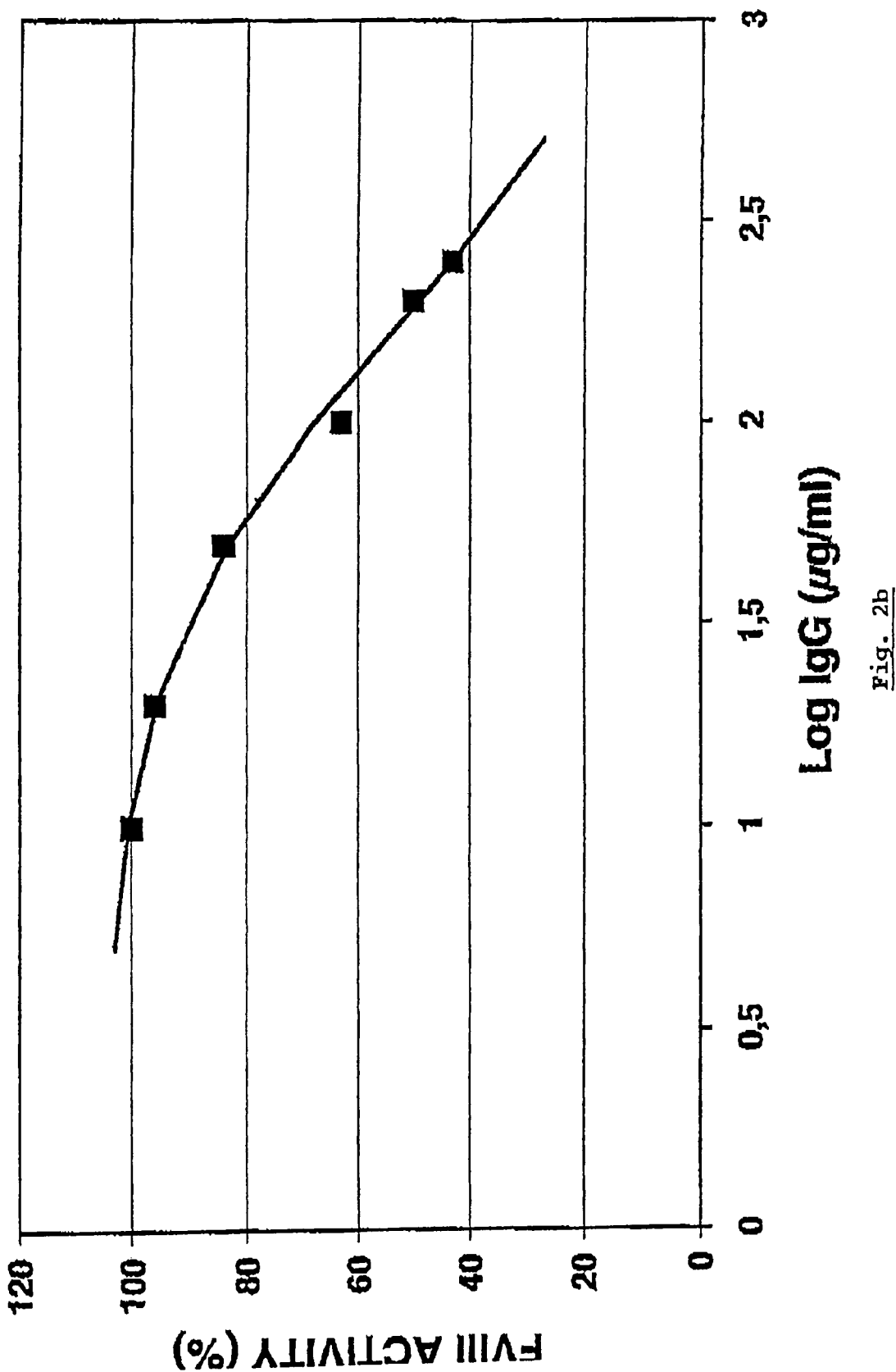

Use of FVIII Peptides for the Immunopurification of Human Anti-FVIII Antibodies in Healthy Donors To prepare and characterize human anti-FVIII antibodies present in healthy individuals, we analyzed Cohn fraction II+III, rich in immunoglobulins, for the presence of selected specific anti-peptide antibodies. Human anti-FVIII-peptide antibodies (HAP1 to HAP11, HAP16 and HAP17) were purified by affinity chromatography on Sepharose coupled to the appropriate peptide (see Table 2). As a typical example, FIG. 2 shows the chromatographic profile obtained with SEQ ID 32, a sequence found in C2 domain. Table 2 summarizes the results obtained with 17 epitopic sequences selected in each FVIII domain (A1, A2, A3, B, C1 and C2). Significant amounts of immunoglobulins, specific for each of the 13 FVIII peptides used, were obtained from the starting plasma fraction II+III. The specificity of the resulting purified human antibodies was directly tested by immunoblotting with plasma FVIII, recombinant FVIII, and the fragments obtained after thrombin proteolysis (see Table 2).

The IgG isotype distribution in the human purified antibody preparations was found to be quite heterogeneous. Interestingly, 40 to 79% of the recovered IgGs belonged to the IgG2 subclass. In most preparations, IgG4 appeared to be over-represented (up to 25%).

All the human anti-FVIII-peptide antibody preparations were tested for the capacity to inhibit FVIII activity in a one-stage clotting assay. Table 2 shows that seven out of 13 preparations tested (54%) displayed inhibitory activity, SEQ ID NO.: 14, SEQ ID NO.: 19, SEQ ID NO.: 2, SEQ ID NO.: 5, SEQ ID NO.: 22, SEQ ID NO.: 32 and SEQ ID NO.: 33, respectively. As a typical example, the inhibition of FVIII activity in function of anti-SEQ ID 32 Ig concentration is shown in FIG. 2.

Human Anti-FVIII-Peptide Ig Immunospecificity Towards FVIII

Figure 3:
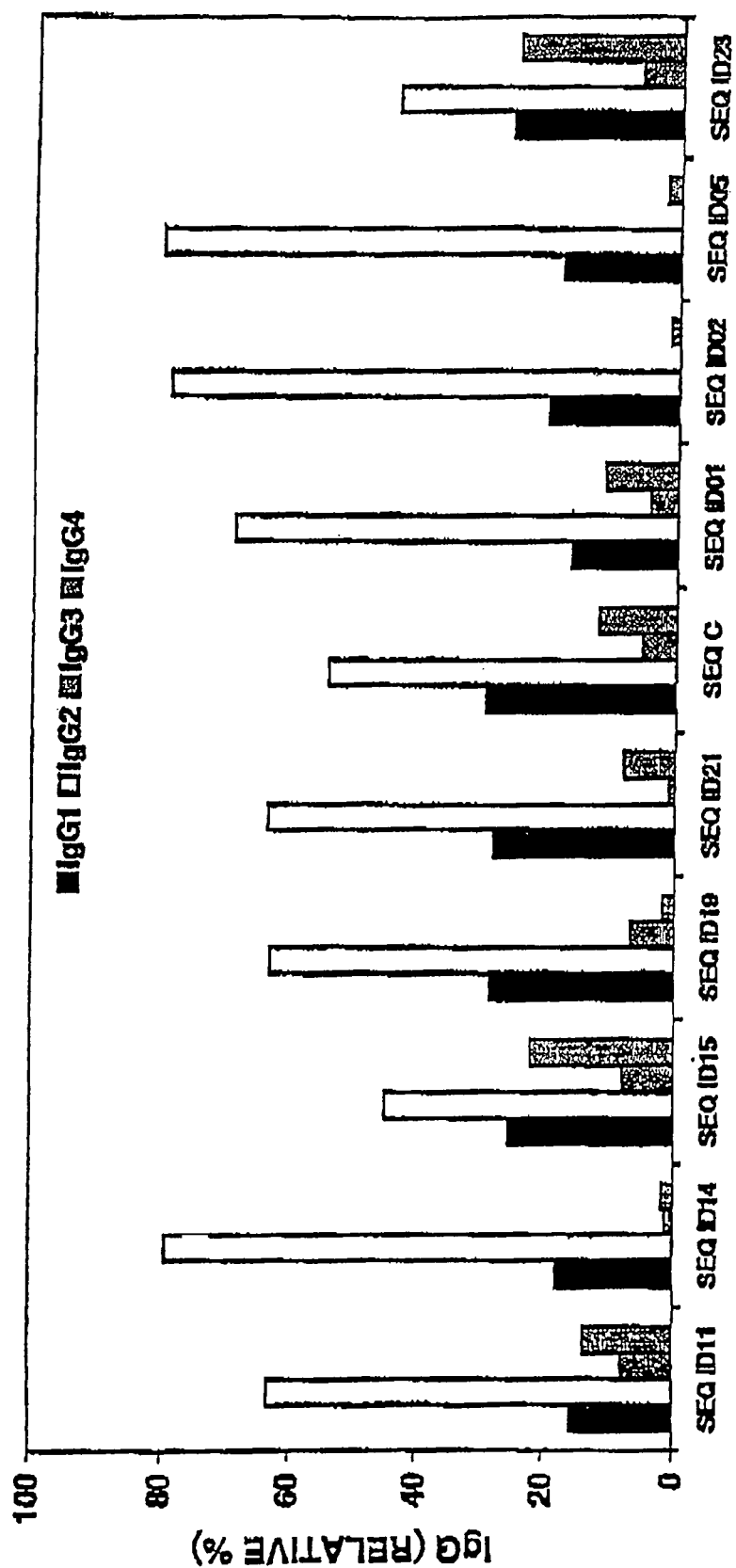
FIG. 3. This figure represents the human anti-peptide antibody immunoreactions with FVIII polypeptides after Western Blotting (panel A from left to right: human antibodies HAP1 through HAP4, specific for different FVIII epitope sequences found in the FVIII HC—see also Table 2 and panel B: human antibodies specific for the P5 peptide and the FVIII LC sequences, P7, P8, and P9—see also Table 2). The RAP9 lane shows the reactivity of FVIII polypeptides towards purified rabbit antibodies specific for the peptide sequence Arg$^{1797}$-Tyr$^{1815}$ (see also Table 2).

The specificity of the resulting purified human antibodies was tested by immunoblotting with plasma FVIII, recombinant FVIII, and the fragments obtained after thrombin proteolysis. Again, the FVIII fragments were identified with either FVIII-HC- or FVIII-LC-specific mouse monoclonal antibodies or FVIII-peptide-specific rabbit polyclonal antibodies. The human antibodies were identified after binding of biotinylated goat anti-human IgG. FIG. 3 shows the immunoreaction of high-molecular-weight FVIII ($\geqq$92-kDa) with four human antibody preparations, purified on Sepharose coupled to FVIII peptide SEQ ID NO.: 11 ($Ser^{109}$-$Lys^{127}$), SEQ ID NO.: 14 ($Cys^{329}$-$Asp^{348}$), SEQ ID NO.: 15 ($Tyr^{407}$-$Lys^{425}$) or SEQ ID NO.: 19 ($Cys^{711}$-$Asp^{725}$). The 50-kDa FVIII fragment (domain A1) was recognized by human antibodies purified on $Ser^{109}$-$Lys^{127}$ or $Cys^{329}$-$Asp^{348}$-Sepharose and the 44-kDa FVIII fragment (A2) by immunoglobulins purified on $Tyr^{407}$-$Lys^{425}$ and $Cys^{711}$-$Asp^{725}$-Sepharose. The lack of reactivity of the anti-($Ser^{817}$-$Ser^{830}$) immunoglobulin preparation (HAP5) with the FVIII fragments confirms that this epitope is located in the amino-terminal end of domain B (FIG. 3). Human antibodies purified on Sepharose coupled to peptide SEQ ID NO.: 1 ($Arg^{1652}$-$Tyr^{1664}$) or SEQ ID NO.: 2 ($Asp^{1681}$-$Arg^{1696}$) reacted strongly with the 80-kDa FVIII light chain (FIG. 3). For both preparations, the reaction with the 80-kDa band disappeared after thrombin proteolysis, indicating that the epitopes, as expected, are located in the a3 acidic peptide at the $NH_2$-terminal part of the FVIII A3 domain. When human antibodies specific for peptide SEQ ID NO.: 5 ($Arg^{1797}$-$Tyr^{1815}$ in A3 domain) were analyzed by immunoblotting, their specificity for rFVIII appeared restricted to the 80-kDa FVIII light chain and its 72-kDa thrombin fragment.

No immunoreaction with the rFVIII chains or fragments was detected with antibody preparations specific for FVIII peptides SEQ C and SEQ ID NO.: 23, although a positive reaction was obtained in the ELISA using rFVIII. This could mean that these immunoglobulin preparations recognize a conformational epitope.

Figure 4:
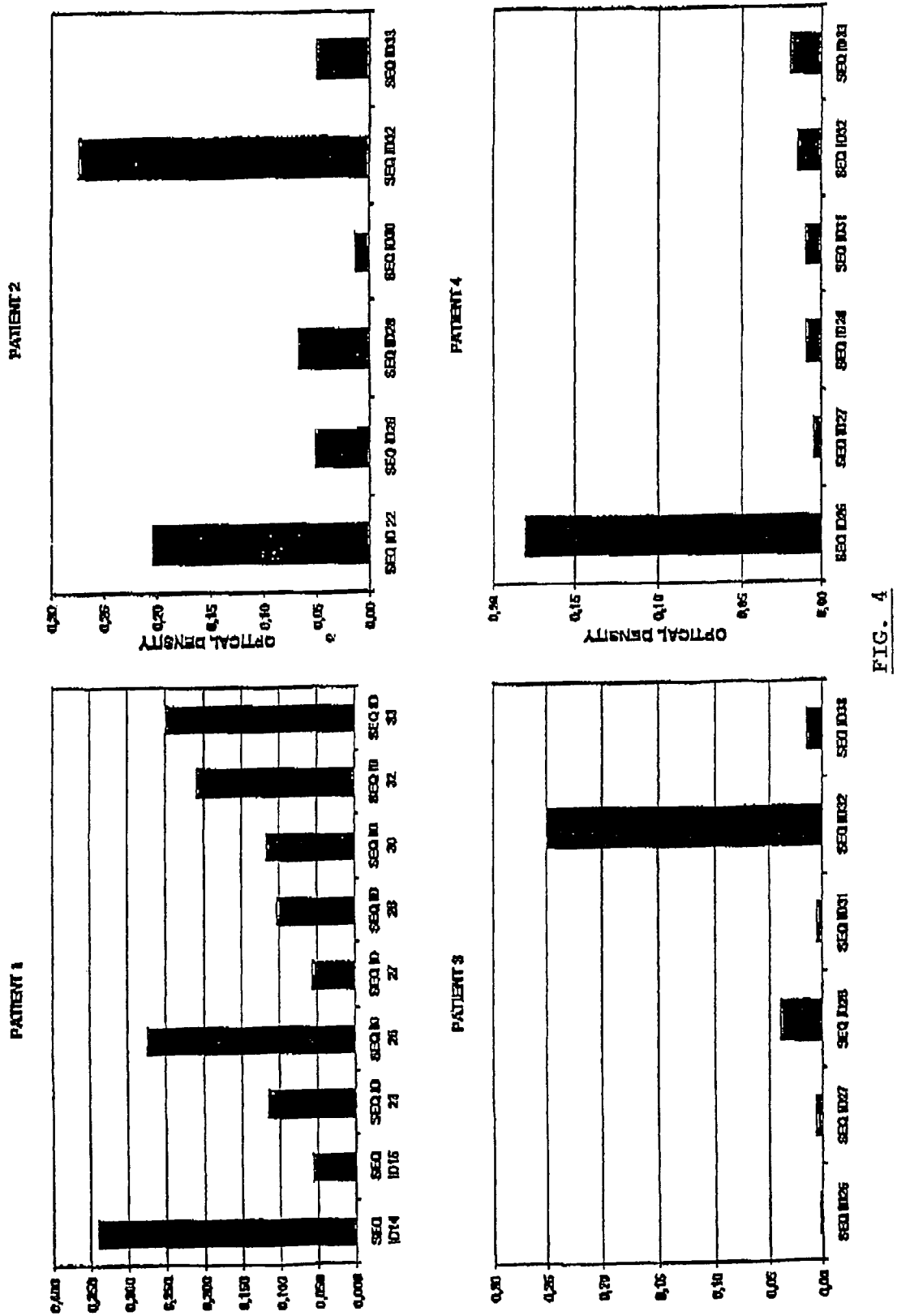
FIG. 4. This figure represents the ELISA reactivity of the four inhibitor plasmas with different peptide sequences. Inhibitors present in four patient plasmas were analyzed by ELISA test using as coated antigens the different selected FVIII epitopes synthetic peptides, as indicated by the ordinate.

Use of FVIII Synthetic Peptides to Characterize Human Anti-FVIII Antibodies in Hemophilia A Patient Plasmas The selected peptides were used in ELISA experiment to determine the anti-FVIII antibody specificity's present in hemophilia A plasmas. The peptides were coated on microplate (25 μg/ml in PBS buffer during 16 h at 4° C.). A 1/10 to 1/1000 dilution of plasma patient in Tris-casein buffer was reacted with the coated peptide for 2 h at 37° C. The bound human IgG was measured as described in Methods. Control samples were plasma pools of healthy donors. FIG. 4 shows the results obtained with the plasma of 4 hemophilia A patients. The optical densities are corrected average values (OD patient-OD normal plasma pool) of two independent experiments.

Molecular Model Epitope Prediction

Pemberton et al (1997) have built a molecular model of the A domains of FVIII. This 3-D model makes it possible to explore predictions for important regions of FVIII activity. The model was used to locate the FVIII-peptide epitopes identified by the Parker and Hodge algorithms. As predicted by these algorithms, all peptides located in the A domains were found on the FVIII surface and were fully accessible to specific.

The overlap between the epitope and the FIXa-binding loop (5 common residues spanning $Glu^{1811}$-$Tyr^{1815}$) may explain the inhibitory action of the corresponding anti-($Arg^{1797}$-$Tyr^{1815}$) antibodies on formation of the fibrin clot.

Analysis

In the clotting test, significant inhibition of FVIII activity was recorded in the presence of rabbit anti-($Cys^{329}$-$Asp^{348}$) and anti-($Arg^{1652}$-$Tyr^{1664}$) antibodies, but different inhibition patterns were observed. Inhibition by anti-($Arg^{1652}$-$Tyr^{1664}$) follows second-order kinetics with a drastic reduction in FVIII activity. Anti-($Cys^{329}$-$Asp^{348}$) Ig is less efficient and shows a more complex type of reaction, with a non-linear dependence on the antibody concentration. Epitope $Arg^{1652}$-$Tyr^{1664}$ and the adjacent major binding site vWF (residues $Glu^{1675}$-$Glu^{1684}$) are located in the acidic light-chain peptide a3. As shown by western blotting, a3 is released from the A3 domain after thrombin treatment, preventing further binding of anti-($Arg^{1652}$-$Tyr^{1664}$) Ig to activated FVIII. Similar results have been reported by Shima et al (1991), who described the FVIII sequence $Asp^{1663}$-$Ser^{1669}$ as a binding site of rabbit polyclonal antibodies neutralizing FVIII activity. Epitope $Cys^{329}$-$Asp^{348}$ overlapped the acidic $Asp^{348}$-$Lys^{362}$ sequence (in a1) described as adjacent to the activated protein C ($Arg^{336}$) and thrombin ($Arg^{372}$) cleavage sites. It is the target of human hemophilic inhibitors. Anti-($Asp^{348}$-$Lys^{362}$) antibodies may interfere with proteolysis or with the FX interaction site ($Met^{337}$-$Arg^{372}$) (Saenko et al., 1999 and Scandella et al., 2000).

FVIII-neutralizing activity was measured in all 13 Ig preparations. Seven human Ig preparations displayed inhibition of procoagulant activity, these being specific for amino-acid residues $Cys^{711}$-$Asp^{725}$, $Tyr^{1681}$-$Arg^{1696}$, and $Arg^{1797}$-$Tyr^{1815}$ respectively. The $Cys^{711}$-$Asp^{725}$ sequence contains sulfated tyrosines at $Tyr^{718}$, $Tyr^{719}$, and $Tyr^{723}$, and overlaps with the FVIII HC region $Lys^{713}$-$Arg^{740}$ described as promoting both activation and HC proteolysis. The additional sulfated groups may be required for proper interaction with thrombin or another component as in the FX-activating complex. The sequence also overlaps with region $Gly^{701}$-$Ser^{750}$, recognized by a weakly inhibitory mouse monoclonal antibody. Peptide P8 ($Tyr^{1681}$-$Arg^{1696}$) (FVIII LC) includes the sequence $Glu^{1684}$-$Arg^{1689}$ already described by Shima et al, 1991. It contains the thrombin activation site $Arg^{1689}$-$Ser^{1690}$. P4 ($Cys^{711}$-$Asp^{725}$) is also included in the $Asp^{712}$-$Ala^{736}$ sequence detected by analysis of the patient antibody repertoire by gene phage display technology. It is proposed as a possible additional inhibitor in patients (van den Brink et al, 2000). Peptide P9 ($Arg^{1797}$-$Tyr^{1815}$) contains the FXa binding site (see below).

Of the 16 anti-FVIII-peptide immunoglobulins purified from humans or produced in rabbits, 7 did neutralize FVIII activity under the tested conditions. Using small peptide sequences and immunobinding assays, we have provided evidence for additional new epitopes. We have located new epitopes in the A1 domain (residues $Ser^{109}$-$Cys^{127}$), the A2 domain ($Cys^{407}$-$Lys^{425}$), and the B domain ($Ser^{817}$-$Ser^{830}$ and $Glu^{1078}$-$Pro^{1092}$).

Autoantibodies immunopurified with denatured FVIII have been reported in healthy subjects and in pools of normal human immunoglobulins (processed fraction II, see above) (Algiman et al., 1992 and Moreau et al., 2000). A possible role in clearance of denatured FVIII or its fragments from the bloodstream and/or in the immunotolerance was suggested.

Identification of the FVIII epitopes is a major challenge to be met in order to improve FVIII treatment and the quality of therapeutic FVIII concentrates. FVIII epitope sequences help to determine the contribution of patient polyclonal anti-FVIII Igs to overall inhibitory and regulatory activity. They could also be used to monitor the usual switch in anti-FVIII specificity in a patient during treatment. Said characterization of FVIII epitopes and a model of their locations on the folded molecule improves the treatment of inhibitors in both hemophilic and non-hemophilic patients (detection, follow-up, therapeutic use of FVIII epitope peptides . . . ).

TABLE 1

Characterization of rabbit anti-FVIII peptides antibodies

| SEQ ID NO(a) | Rabbit Antiserum(b) | ELISA Titer(c) P-KLH | ELISA Titer(c) r-FVIII | FVIII domain recognize(d) | RAP-IgG Recovery(e) µg/ml serum | Inhibitor Titer(f) BU/mg |
|---|---|---|---|---|---|---|
| 11 | RAP1 | 2.5 | 2.2 | A1 | 27 | — |
| 14 | RAP2 | 3.6 | 2.5 | A1/a1 | 55 | 1.5 |
| 15 | RAP3 | 2.5 | 3.2 | A2 | 268 | — |
| 19 | RAP4 | 2.5 | 1.3 | A2/a2 | 12 | — |
| 21 | RAP5 | 4.6 | 3.9 | B | 106 | — |
| C | RAP6 | 3.8 | 2.9 | — | 14 | — |
| 01 | RAP7 | 3.9 | 3.9 | a3 ↓ | 35 | 0.5 |
| 02 | RAP8 | 1.9 | 0.9 | a3/A3 ↓ | 3 | — |
| 05 | RAP9 | 3.8 | 2.6 | A3 | 42 | — |
| 23 | RAP10 | 3.9 | 0.8 | — | 65 | — |
| 22 | RAP11 | ND | ND | ND | ND | ND |
| 26 | RAP12 | 4.1 | 1.1 | C2 | ND | ND |
| 27 | RAP13 | 3.7 | 1.1 | C2 | ND | ND |
| 28 | RAP14 | 3.8 | 0.9 | C2 | ND | ND |
| 31 | RAP15 | 3.2 | 0.7 | C2 | ND | ND |
| 32 | RAP16 | 3.5 | 1.8 | C2 | ND | ND |
| 33 | RAP17 | 4.8 | 1.2 | C2 | ND | ND |

TABLE 2

Characterization of human anti-FVIII peptides autoantibodies

| SEQ ID(a) | Human Anti-peptide Ig(b) | FVIII reactivity on immunoblot (−thrombin)(c) | FVIII reactivity on immunoblot (+thrombin)(d) | FVIII domain(e) | HAP-IgG Recovery(f) µg/10 mg IgG | FVIII inhibitory Activity(g) BU/mg |
|---|---|---|---|---|---|---|
| SEQ ID 11 | HAP1 | >92 kDa | 50 kDa | A1 | 0.27 | — |
| SEQ ID 14 | HAP2 | >92 kDa | 50 kDa | A1/a1 | 1.07 | 3.4 |
| SEQ ID 15 | HAP3 | >92 kDa | 44 kDa | A2 | 0.06 | — |
| SEQ ID 19 | HAP4 | 92 kDa | 44 kDa | A2/a2 | 0.12 | + |
| SEQ ID 21 | HAP5 | >100 kDa | — | B | 0.26 | — |
| SEQ C | HAP6 | — | — | — | 0.03 | — |
| SEQ ID 01 | HAP7 | 80 kDa | 80 kDa | a3 ↓ | 0.20 | — |
| SEQ ID 02 | HAP8 | 80 kDa | 80 kDa | a3/A3 ↓ | 0.01 | + |
| SEQ ID 05 | HAP9 | 80 kDa | 72 kDa | A3 | 0.08 | + |
| SEQ ID 23 | HAP10 | — | — | — | 0.11 | — |
| SEQ ID 22 | HAP11 | ND | ND | ND | 0.98 | 4.3 |
| SEQ ID 26 | HAP12 | ND | ND | ND | ND | ND |
| SEQ ID 27 | HAP13 | ND | ND | ND | ND | ND |
| SEQ ID 28 | HAP14 | ND | ND | ND | ND | ND |
| SEQ ID 31 | HAP15 | ND | ND | ND | ND | ND |
| SEQ ID 32 | HAP16 | 80 kDa | 72 kDa | A3C1C2 | 2.40 | 6.3 |
| SEQ ID 33 | HAP17 | ND | ND | ND | 1.06 | 2.4 |

+: Inhibition >25% at 100 µg/ml

REFERENCES

The disclosures of the following references are incorporated herein by reference in their entireties.

1. Algiman, M., et al. (1992) Proc Natl Acad Sci USA. 89, 3795-3799
2. Dietrich, G., et al. (1992), Blood 79, 2946-2951
3. Ewenstein, B. M., et al. (2000), Haematologica 85 (suppl. 10), 35-39
4. Foster, P A and Zimmerman, T. S. (1989), Blood Reviews 3, 190-191
5. Janin, J. (1979) Nature 277, 491-492
6. Karplus, P A and Schulz, G E. (1985) Naturwissenschaften 72, 212
7. Knobf, P. and Derfler, K (1999), Vox Sanguinis 77 (suppl. 1), 57-64
8. Laub, R., et al. (1999) Thromb Haemost. 81, 39-44
9. Lollar P. (2000), Haematol. 85 (suppl 10), 26-30
10. Moreau, A., et al. (2000) Blood 95, 3435-3441
11. Morrisson and Ludlam. (1995), Br J Haematol. 89, 231-6
12. Palmer, D S, et al. (1997) Vox Sang. 72, 148-161
13. Parker, J M R, et al. (1986) Biochem. 25, 5425-5432
14. Peerlinck, K. et al. (1997), Thromb Haemost 77, 80-86
15. Pemberton, S., et al. (1997), Blood 89, 2413-2421
16. Pratt K P. (2000), Curr. Opinion Drug Discovery & Development 3, 516-526
17. Raut, S., et al. (1998), Thromb Haemost. 80, 624-631
18. Reding, M T, et al. (2000), Thromb Haemost. 84, 643-52
19. Reisner, H M, et al. In: Aledort L M et al, eds. Inhibitors to coagulation factors. New York, N.Y.: Plenum Press (1995), 65-78
20. Saenko, E L, et al. (1999), TCM 9, 185-192
21. Scandella, D. (2000), Semin Thromb Haemost. 26, 137-142
22. Shima, M., et al. (1991), Int J Haematol. 54, 515-522

23. Toole et al. (1984) Nature 312, 342-7
24. Tuddenham, E G and McVey, J H. (1998) Hemophilia 4, 543-545
25. van den Brink, E N, et al. (2000) Blood. 96, 540-545
26. Van Regenmortel, Methods: A companion to Methods in Enzymology, 9, page 465-472, 1996
27. Verhar et al. (1984) Nature 312, 339
28. Vermylen J. (1998), Hemophilia 4, 538-542.

What is claimed is:

1. An isolated or purified antigenic fragment of a human factor VIII polypeptide, the fragment consisting of SEQ ID NO: 32.

2. A complex comprising a carrier protein or a carrier peptide linked to the antigenic fragment according to claim 1.

3. A pharmaceutical composition comprising an adequate pharmaceutical carrier and the antigenic fragment of claim 1.

4. A purification or diagnostic device comprising a solid support attached to the isolated or purified antigenic fragment of a human factor VIII polypeptide of claim 1.

5. The purification or diagnostic device of claim 4, wherein said purification device is a chromatography column or filter.

6. A purification or diagnostic device comprising a solid support attached to the complex of claim 2.

7. The purification or diagnostic device of claim 6, wherein said purification device is a chromatography column or filter.

8. An isolated or purified antigenic fragment of a human factor VIII polypeptide having up to 25 amino acids, wherein the fragment consists essentially of SEQ ID NO: 32 and is recognized by anti-human factor VIII antibodies.

9. A method of obtaining a factor VIII inhibitor, comprising:
    passing a physiological liquid over a solid support comprising the fragment of a human factor VIII polypeptide of claim 1 to capture a factor VIII inhibitor or fragment thereof; and
    eluting the captured factor VIII inhibitor or fragment thereof from said solid support.

10. The method of claim 9, wherein said factor VIII inhibitor is a human anti-factor VIII antibody.

11. The method of claim 9, wherein said physiological liquid is serum, plasma or blood.

12. The method of claim 9, wherein said solid support is a chromatography column or filter.

13. The method of claim 9, wherein said fragment of a factor VIII polypeptide is linked to a carrier protein or a carrier peptide.

14. The method of claim 10, further comprising collecting the fraction containing said factor VIII anti-factor VIII antibody.

15. A method of obtaining a factor VIII inhibitor, comprising:
    passing a physiological liquid over a solid support comprising the fragment of a human factor VIII polypeptide of claim 8 to capture a factor VIII inhibitor or fragment thereof; and
    eluting the captured factor VIII inhibitor or fragment thereof from said solid support.

16. The method of claim 15, wherein said factor VIII inhibitor is a human anti-factor VIII antibody.

17. The method of claim 15, wherein said physiological liquid is serum, plasma or blood.

18. The method of claim 15, wherein said solid support is a chromatography column or filter.

19. The method of claim 15, wherein said fragment of a factor VIII polypeptide is linked to a carrier protein or a carrier peptide.

20. The method of claim 16, further comprising collecting the fraction containing said anti-factor VIII antibody.

21. A method of removing a factor VIII inhibitor from a physiological liquid, comprising:
    passing a physiological liquid over a solid support comprising the fragment of a human factor VIII polypeptide of claim 1 to capture a factor VIII inhibitor or fragment thereof;
    removing said factor VIII inhibitor from said physiological liquid by capturing said factor VIII inhibitor or fragment thereof on said solid support; and
    obtaining physiological liquid from which said factor VIII inhibitor has been removed.

22. The method of claim 21, wherein said factor VIII inhibitor is a human anti-factor VIII antibody.

23. The method of claim 21, wherein said physiological liquid is serum, plasma or blood.

24. The method of claim 21, wherein said solid support is a chromatography column or filter.

25. The method of claim 21, wherein said fragment of a factor VIII polypeptide is linked to a carrier protein or a carrier peptide.

26. A method of introducing to a patient a physiological liquid from which a factor VIII inhibitor has been removed, comprising:
    passing a physiological liquid from a patient over a solid support comprising the fragment of a human factor VIII polypeptide of claim 1 to capture a factor VIII inhibitor or fragment thereof;
    capturing said factor VIII inhibitor or fragment thereof on said solid support;
    obtaining physiological liquid from which said factor VIII inhibitor has been removed; and
    administering to said patient said physiological liquid from which said factor VIII inhibitor has been removed.

27. The method of claim 26, wherein said factor VIII inhibitor is a human anti-factor VIII antibody.

28. The method of claim 26, wherein said physiological liquid is serum, plasma or blood.

29. The method of claim 26, wherein said solid support is a chromatography column or filter.

30. The method of claim 26, wherein said fragment of a factor VIII polypeptide is linked to a carrier protein or a carrier peptide.

31. A method of removing a factor VIII inhibitor from a physiological liquid, comprising:
    passing a physiological liquid over a solid support comprising the fragment of a human factor VIII polypeptide of claim 8 to capture a factor VIII inhibitor or fragment thereof;
    removing said factor VIII inhibitor from said physiological liquid by capturing said factor VIII inhibitor or fragment thereof on said solid support; and
    obtaining physiological liquid from which said factor VIII inhibitor has been removed.

32. The method of claim 31, wherein said factor VIII inhibitor is a human anti-factor VIII antibody.

33. The method of claim 31, wherein said physiological liquid is serum, plasma or blood.

34. The method of claim 31, wherein said solid support is a chromatography column or filter.

35. The method of claim 31, wherein said fragment of a factor VIII polypeptide is linked to a carrier protein or a carrier peptide.

36. A method of introducing to a patient a physiological liquid from which a factor VIII inhibitor has been removed, comprising:
    passing a physiological liquid from a patient over a solid support comprising the fragment of a human factor VIII polypeptide of claim 8 to capture a factor VIII inhibitor or fragment thereof;
    capturing said factor VIII inhibitor or fragment thereof on said solid support;
    obtaining physiological liquid from which said factor VIII inhibitor has been removed; and administering to said patient said physiological liquid from which said factor VIII inhibitor has been removed.

37. The method of claim 36, wherein said factor VIII inhibitor is a human anti-factor VIII antibody.

38. The method of claim 36, wherein said physiological liquid is serum, plasma or blood.

39. The method of claim 36, wherein said solid support is a chromatography column or filter.

40. The method of claim 36, wherein said fragment of a factor VIII polypeptide is linked to a carrier protein or a carrier peptide.

41. A method for detecting factor VIII inhibitors in a subject, comprising the steps of contacting a physiologic fluid of a subject with the antigenic fragment of claim 1 and detecting the binding of inhibitors present in said physiologic fluid to said epitope.

42. The method according to claim 41, wherein said inhibitor is an anti-factor VIII antibody.

43. The method according to claim 41, wherein said physiological fluid is serum, plasma or blood.

44. A method for detecting factor VIII inhibitors in a subject, comprising the steps of contacting a physiologic fluid of a subject with the antigenic fragment of claim 8 and detecting the binding of inhibitors present in said physiologic fluid to said epitope.

45. The method according to claim 44, wherein said inhibitor is an anti-factor VIII antibody.

46. The method according to claim 44, wherein said physiological fluid is serum, plasma or blood.

47. The antigenic fragment of claim 1, wherein said antigenic fragment is derived from recombinant FVIII, synthetic FVIII, or from plasma FVIII.

48. The antigenic fragment of claim 8, wherein said antigenic fragment is derived from recombinant FVIII, synthetic FVIII, or from plasma FVIII.

49. A complex comprising a carrier protein or a carrier peptide linked to the antigenic fragment according to claim 8.

50. A pharmaceutical composition comprising an adequate pharmaceutical carrier and the antigenic fragment of claim 8.

51. A purification or diagnostic device comprising a solid support attached to the isolated or purified antigenic fragment of a human factor VIII polypeptide of claim 8.

52. The purification or diaganostic device of claim 51, wherein said purification device is a chromatography column or filter.

53. A purification or diagnostic device comprising a solid support attached to the complex of claim 49.

54. The purification or diagnostic device of claim 53, wherein said purification device is a chromatography column or filter.

* * * * *